US011779411B2

(12) United States Patent
Suzuki et al.

(10) Patent No.: US 11,779,411 B2
(45) Date of Patent: Oct. 10, 2023

(54) OPERATION SYSTEM, SURGICAL SYSTEM, CONTROL DEVICE, DISTORTION GENERATING BODY, SURGICAL INSTRUMENT, AND EXTERNAL FORCE DETECTING SYSTEM

(71) Applicant: Sony Corporation, Tokyo (JP)

(72) Inventors: Hiroyuki Suzuki, Tokyo (JP); Kenichiro Nagasaka, Tokyo (NA)

(73) Assignee: SONY CORPORATION, Tokyo (JP)

( * ) Notice: Subject to any disclaimer, the term of this patent is extended or adjusted under 35 U.S.C. 154(b) by 631 days.

(21) Appl. No.: 16/490,596

(22) PCT Filed: Feb. 2, 2018

(86) PCT No.: PCT/JP2018/003618
§ 371 (c)(1),
(2) Date: Sep. 3, 2019

(87) PCT Pub. No.: WO2018/163680
PCT Pub. Date: Sep. 13, 2018

(65) Prior Publication Data
US 2019/0388165 A1 Dec. 26, 2019

(30) Foreign Application Priority Data
Mar. 10, 2017 (JP) .................. 2017-046788

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/29* (2013.01); *A61B 34/71* (2016.02); *A61B 34/76* (2016.02);
(Continued)

(58) Field of Classification Search
CPC ......... A61B 34/30; A61B 17/29; A61B 34/71; A61B 34/76; A61B 90/50; A61B 17/295;
(Continued)

(56) References Cited

U.S. PATENT DOCUMENTS

2001/0021843 A1 9/2001 Bosselmann et al.
2007/0151391 A1* 7/2007 Larkin .................. A61B 34/76
74/490.06
(Continued)

FOREIGN PATENT DOCUMENTS

| CN | 101340850 A | 1/2009 |
|---|---|---|
| JP | 7-60683 A | 3/1995 |
| JP | 2016-74060 A | 5/2016 |

OTHER PUBLICATIONS

International Search Report and Written Opinion dated May 1, 2018 for PCT/JP2018/003618 filed on Feb. 2, 2018, 7 pages including English Translation of the International Search Report.
(Continued)

*Primary Examiner* — Timothy J Neal
*Assistant Examiner* — Uyen N Vo
(74) *Attorney, Agent, or Firm* — XSENSUS LLP

(57) ABSTRACT

An operation system, a surgical system, a control device, a distortion generating body, a surgical instrument and the like for detecting a force acting on an end effector are provided. The surgical system includes an arm including one or more links, an end effector arranged at a tip end of the arm, a first distortion detecting unit that detects distortion generated in the end effector, a second distortion detecting unit that detects distortion generated in the link, and a processing unit that calculates a force acting on the end effector in a living body on the basis of detection results of the first distortion detecting unit and the second distortion detecting unit.

9 Claims, 14 Drawing Sheets

(51) Int. Cl.
*A61B 90/50* (2016.01)
*A61B 17/29* (2006.01)
*B25J 9/10* (2006.01)
*A61B 90/00* (2016.01)
*A61B 17/295* (2006.01)

(52) U.S. Cl.
CPC ............ *A61B 90/50* (2016.02); *A61B 17/295* (2013.01); *A61B 2017/2926* (2013.01); *A61B 2034/305* (2016.02); *A61B 2090/064* (2016.02); *B25J 9/106* (2013.01)

(58) Field of Classification Search
CPC ...... A61B 2017/2926; A61B 2034/305; A61B 2090/064; A61B 2034/2061; A61B 2034/301; A61B 34/37; B25J 9/106; B25J 9/1638; G05B 19/0426; G05B 2219/45117
See application file for complete search history.

(56) References Cited

U.S. PATENT DOCUMENTS

| | | | | |
|---|---|---|---|---|
| 2010/0087835 | A1* | 4/2010 | Blumenkranz | A61B 90/10 606/130 |
| 2011/0251605 | A1* | 10/2011 | Hoarau | A61B 5/4875 606/41 |
| 2013/0116706 | A1 | 5/2013 | Lee | |
| 2014/0012286 | A1* | 1/2014 | Lee | A61B 34/37 606/130 |
| 2014/0067123 | A1* | 3/2014 | Park | A61B 34/30 73/862.041 |

OTHER PUBLICATIONS

Seibold et al., "Prototype of Instrument for Minimally Invasive Surgery with 6-Axis Force Sensing Capability", Proceedings of the 2005 IEEE, International Conference on Robotics and Automation, Barcelona, Spain, Apr. 2005, pp. 498-503.

* cited by examiner

FIG. 3
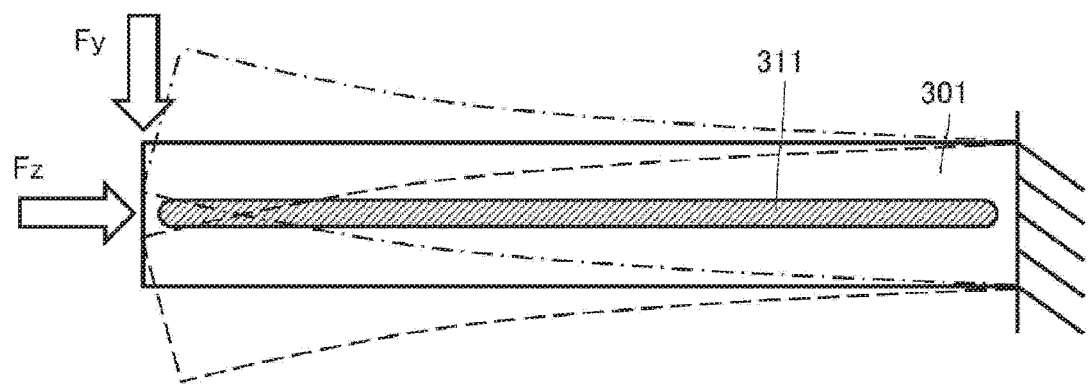
(A)
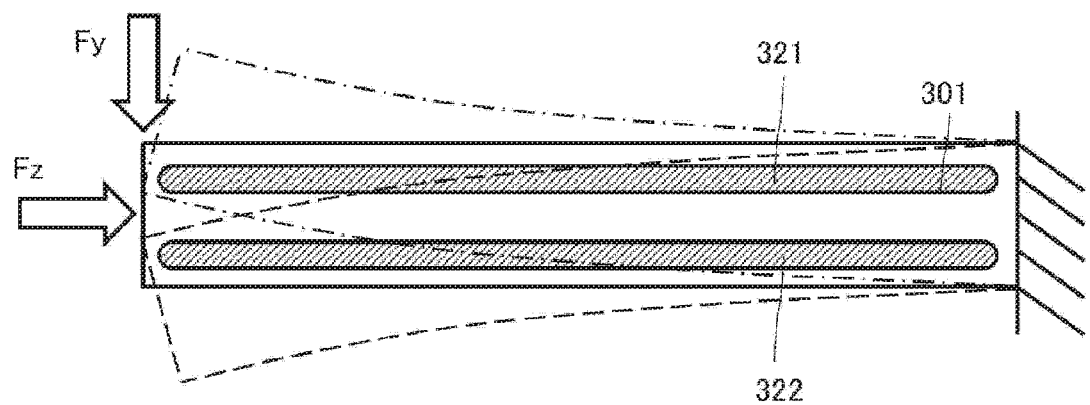
(B)

OPERATION SYSTEM, SURGICAL SYSTEM, CONTROL DEVICE, DISTORTION GENERATING BODY, SURGICAL INSTRUMENT, AND EXTERNAL FORCE DETECTING SYSTEM

CROSS-REFERENCE TO RELATED APPLICATIONS

The present application is based on PCT filing PCT/JP2018/003618, filed Feb. 2, 2018, which claims priority to JP 2017-046788, filed Mar. 10, 2017, the entire contents of each are incorporated herein by reference.

TECHNICAL FIELD

The technology disclosed in this specification relates to an operation system, a surgical system, a control device, a distortion generating body, a surgical instrument, and an external force detecting system for detecting a force acting on an end effector.

BACKGROUND ART

Recent advances in robotics technology are remarkable, and the robotics technology is widely used in work sites in various industrial fields. For example, in a master-slave robot system, a human (operator) may operate a master arm at hand and a remote slave arm may trace motion thereof, thereby realizing remote operation of a manipulator. The master-slave robot system is used in industrial fields where computer-controlled fully autonomous operation is still difficult, such as a medical robot.

For example, "da Vinci Surgical System (da Vinci)" from Intuitive Surgical, Inc. in USA is a master-slave operation robot first developed for endoscopic surgery of abdominal cavity and chest cavity. The da Vinci is equipped with various types of robot forceps, and an operator may operate by remotely operating the slave arm while obtaining an operation field while watching a three-dimensional monitor screen.

In this master-slave robot system, some proposals are made also for medical robotics systems capable of detecting a force acting on an end effector such as a gripping unit (gripper) (for example, refer to Non-Patent Document 1).

In the operation robot used for endoscopic surgery, it is essential to miniaturize a configuration of the end effector, and a driving mechanism to transmit a driving force generated by a driving unit such as an actuator arranged apart from the end effector by a cable, thereby opening/closing the end effector is common. In the above-described force-detectable medical robotics system, a force sensor is arranged between the end effector and the driving unit that drives the end effector. In such configuration, a pulling force of the cable for opening and closing the end effector interferes with an external force applied in a long axis direction of the end effector, for example, so that there is a fear that deterioration in sensitivity of the force sensor occurs or calibration becomes difficult.

CITATION LIST

Non-Patent Document

Non-Patent Document 1: Ulrich Seibold et al. "Prototype of Instrument for Minimally Invasive Surgery with 6-Axis Force Sensing Capability". Proceedings of the 2005 IEEE International Conference on Robotics and Automation Barcelona, Spain, April 2005, pp. 498-503

SUMMARY OF THE INVENTION

Problems to be Solved by the Invention

An object of the technology disclosed in this specification is to provide excellent operation system, surgical system, control device, distortion generating body, surgical instrument, and external force detecting system capable of preferably detecting a force acting on an end effector.

Solutions to Problems

The technology disclosed in this specification is made in consideration of the above-described problems, and a first aspect thereof is an operation system including:

an arm including one or more links;

an end effector arranged at a tip end of the arm;

a first distortion detecting unit that detects distortion generated in the end effector;

a second distortion detecting unit that detects distortion generated in the link; and a processing unit that calculates a force acting on the end effector on the basis of detection results of the first distortion detecting unit and the second distortion detecting unit.

The end effector includes a forceps unit including a first blade, a second blade, and a joint that defines a forceps rotational axis, the joint coupling the first blade and the second blade so as to be rotatable with respect to each other around the forceps rotational axis.

The first distortion detecting unit includes distortion detecting elements that detect distortion generated on an inner side and an outer side of the first blade, and distortion detecting elements that detect distortion generated on an inner side and an outer side of the second blade. Specifically, the first distortion detecting unit includes distortion detecting elements including FBG sensors formed on optical fibers attached to the inner side and the outer side of the first blade, and distortion detecting elements including FBG sensors formed on optical fibers attached to the inner side and the outer side of the second blade.

Then, the processing unit is configured to calculate a force acting on the end effector on the basis of the distortion on the inner side and the outer side of the first blade and the distortion on the inner side and the outer side of the second blade which are detected.

Furthermore, the second distortion detecting unit includes distortion detecting elements arranged at two locations on opposite sides in two directions orthogonal to a long axis direction of the link. Specifically, the second distortion detecting unit includes the distortion detecting elements including FBG sensors formed in the two locations of optical fibers attached to the opposite sides in the two directions orthogonal to the long axis direction of the link. Then, the processing unit obtains an average value of detection values of the distortion detecting elements, multiplies a result obtained by subtracting the average value from the detection values of the distortion detecting elements by a predetermined calibration matrix, and calculates translational forces and moments in the two directions acting on the end effector.

Furthermore, a second aspect of the technology disclosed in this specification is a surgical system including:

a master device; and a slave device remotely operated by the master device, the slave device including:

an arm including one or more links;

an end effector arranged at a tip end of the arm:

a first distortion detecting unit that detects distortion generated in the end effector;

a second distortion detecting unit that detects distortion generated in the link;

a processing unit that calculates a force acting on the end effector on the basis of detection results of the first distortion detecting unit and the second distortion detecting unit; and an output unit that outputs a processing result by the processing unit to the master device.

Furthermore, a third aspect of the technology disclosed in this specification is a control device including:

a processing unit that calculates a force acting on an end effector on the basis of distortion generated on the end effector arranged at a tip end of an arm and distortion generated on a link forming the arm.

Furthermore, a fourth aspect of the technology disclosed in this specification is a distortion generating body including:

a structure body formed as a blade of a forceps; and a distortion generating unit obtained by forming a meander structure in a long axis direction of the structure body, in which distortion detecting elements are attached on an inner side and an outer side of an opening/closing structure of the forceps of the distortion generating unit.

Furthermore, a fifth aspect of the technology disclosed in this specification is a surgical instrument including:

an arm including one or more links:

an end effector arranged at a tip end of the arm;

a first distortion detecting unit that detects distortion generated in the end effector;

a second distortion detecting unit that detects distortion generated in the link; and a transmitting unit that transmits detection results of the first distortion detecting unit and the second distortion detecting unit.

Furthermore, a sixth aspect of the technology disclosed in this specification is an external force detecting system including:

an arm including one or more links;

an end effector arranged at a tip end of the arm;

a first distortion detecting unit that detects distortion generated in the end effector;

a second distortion detecting unit that detects distortion generated in the link; and a processing unit that calculates a force acting on the end effector on the basis of detection results of the first distortion detecting unit and the second distortion detecting unit.

Effects of the Invention

According to the technology disclosed in this specification, excellent operation system, surgical system, control device, distortion generating body, surgical instrument, and external force detecting system capable of preferably detecting a force acting on the end effector may be provided. The technology disclosed in this specification may be preferably applied to, for example, a medical or operation robot device.

Note that, the effect described in this specification is illustrative only and the effect of the present invention is not limited to this. Furthermore, there also is a case in which the present invention further has an additional effect in addition to the above-described effect.

Still another object, feature, and advantage of the technology disclosed in this specification will become clear by further detailed description with reference to an embodiment to be described later and the attached drawings.

BRIEF DESCRIPTION OF DRAWINGS

FIG. 3 is a view for explaining a scheme for detecting the force acting on the end effector 110.

MODE FOR CARRYING OUT THE INVENTION

An embodiment of a technology disclosed in this specification is hereinafter described in detail with reference to the drawings.

Figure 1:
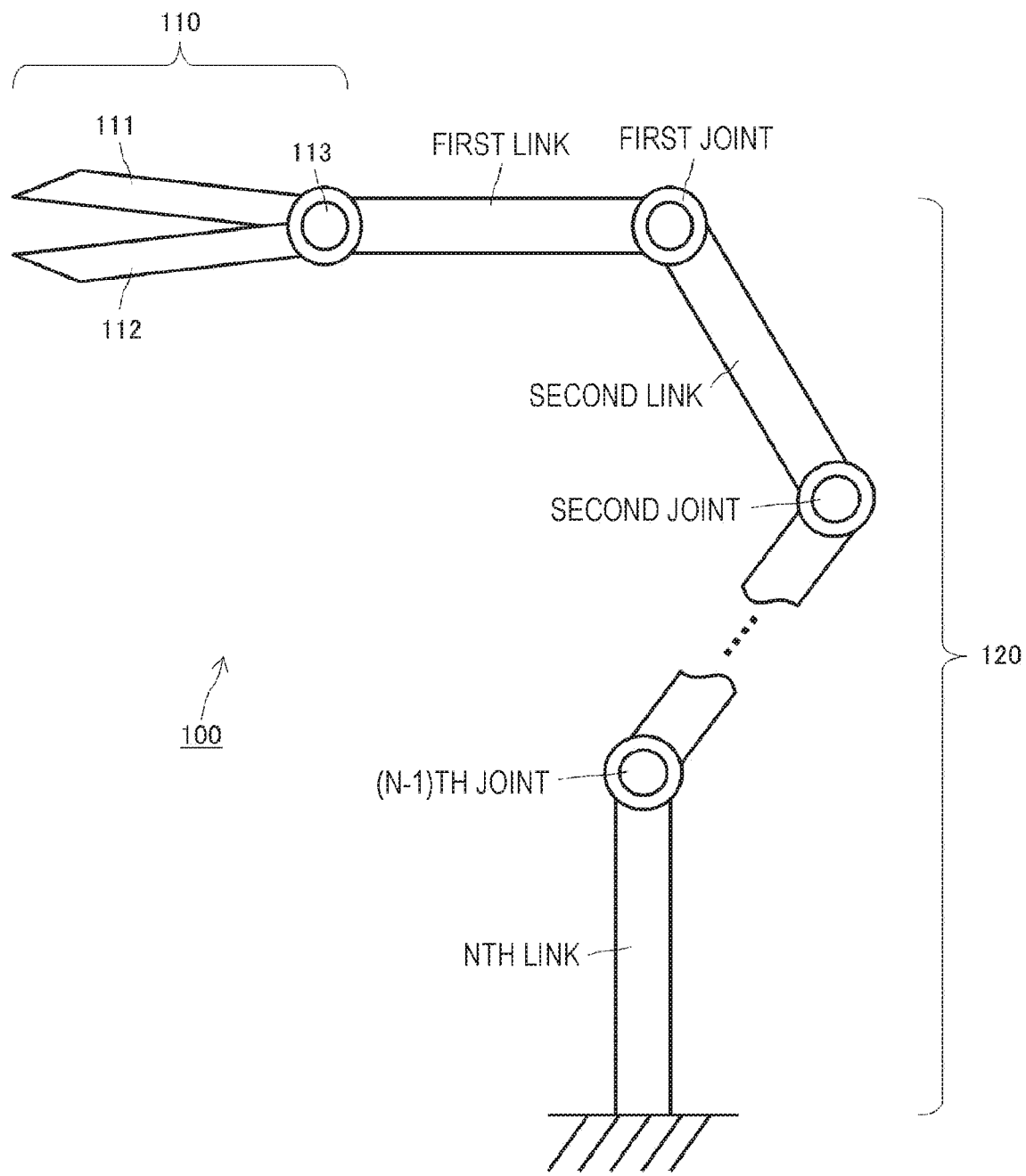
FIG. 1 is a view schematically illustrating a configuration example of a surgical system 100.

FIG. 1 schematically illustrates a configuration example of a surgical system 100 to which the technology disclosed in this specification may be applied. The illustrated surgical system 100 includes an end effector 110 capable of performing opening/closing operation and an articulated arm 120 to a tip end of which the end effector 110 is attached. The surgical system 100 is, for example, a medical or operation system operating as a slave in a master-slave robot system used in eye surgery, brain surgery, and endoscopic surgery of abdominal cavity and chest cavity. In the master-slave robot system, information of a position of a slave arm, an external force applied to the slave arm and the like is desirably fed back in order for an operator to remotely operate the slave arm correctly and efficiently without damaging a target using the master device.

A configuration of the articulated arm 120 such as the number of axes (or the number of joints), a freedom degree configuration of each axis, and the number of links (or the number of arms) is arbitrary. Hereinafter, for convenience of description, links included in the articulated arm 120 are referred to as a first link, a second link, ... sequentially from a distal end (or a rear end of the end effector 110). Furthermore, joints included in the articulated arm 120 are referred to as a first joint, a second joint, ... sequentially from the distal end (or the rear end of the end effector 110).

The end effector 110 is a forceps unit including a pair of blades including a first blade 111 and a second blade 112, and a joint that defines a forceps rotational axis 113, the joint coupling the pair of blades so as to be rotated with respect to each other around the forceps rotational axis. When the first blade 111 and the second blade rotate about the forceps rotational axis 113 so as to be rotated with respect to each other around the forceps rotational axis, the forceps unit 110 may open and close to grip, push-open, and hold a target such as internal tissue or surgical tools. The first blade 111 and the second blade 112 may be coupled so as to be rotatable with respect to each other by forming the forceps rotational axis 113 using, for example, an appropriate gear mechanism. However, since a structure itself of the gear mechanism is not directly related to the technology disclosed in this specification, detailed description thereof is omitted.

The forceps unit 110 is preferably formed as an elongated tube part used by being inserted into a living body such as the abdominal cavity or the chest cavity and made compact as much as possible. It may be said that a distal end of the surgical system 100 is the end effector 110 formed by an elongated tube part, and a proximal end is a mechanical structure coupled to a drive unit of the articulated arm 120 and the like.

In order to make the forceps unit 110 as small as possible, a driving unit (not illustrated) such as an actuator serving as a driving source of the forceps unit 110 is arranged apart from the end effector. Then, a driving force generated by the driving unit is transmitted to each of the first blade and the second blade by a cable (not illustrated), and the first blade 111 and the second blade may rotate about the forceps rotational axis 113 with respect to each other. As a result, the forceps unit 110 may open and close to grip, push-open, or hold the target such as the internal tissue or the surgical instrument. Furthermore, a driving unit serving as a driving source of the first joint is also arranged separately, and the first joint rotates to operate by a pulling force of the cable.

Figure 2:
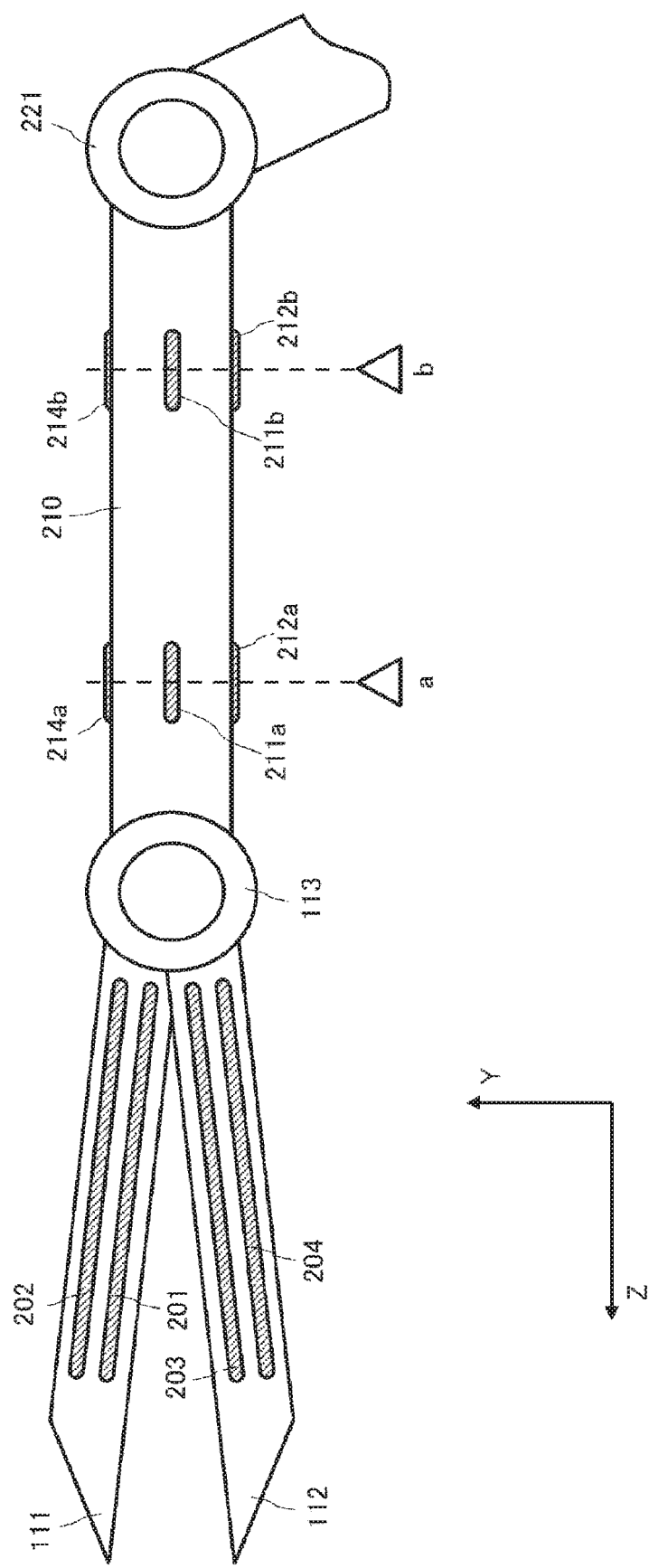
FIG. 2 is a view schematically illustrating a configuration for detecting a force acting on an end effector 110.

FIG. 2 schematically illustrates a configuration for detecting a force acting on the end effector 110 in the surgical system 10) illustrated in FIG. 1. An XYZ coordinate system in which a long axis direction of the end effector 110 is a Z axis is set. Therefore, a leftward direction on a plane of paper is the Z axis, a direction perpendicular to the plane of paper is an X axis, and a vertical direction on the plane of paper is a Y axis.

The first blade 111 may be considered as a cantilever having the forceps rotational axis 113 as a fixed end. Therefore, a pair of distortion detecting elements including a distortion detecting element 201 for detecting distortion on an inner side of an opening/closing structure and a distortion detecting element 202 for detecting distortion on an outer side of the opening/closing structure of the first blade 111 is attached to the first blade 111 so that a distortion amount of the first blade 111 which bends like the cantilever when a force acts may be detected. Note that although the first blade 111 is illustrated to have a simple blade shape in FIG. 2, a distortion generating body is formed on at least a part of the first blade 111 so that the distortion is easily detected (to be described later).

Here, a reason that the pair of distortion detecting elements 201 and 202 is attached to the first blade 111 is described with reference to FIG. 3.

As illustrated in FIG. 3(A), in a case where only one distortion detecting element 311 is attached to a cantilever 301, when an external force Fz in the Z direction is applied to the cantilever 301, the distortion detecting element 311 compresses, so that the external force Fz may be measured. However, since the distortion detecting element 311 extends regardless of whether the cantilever 301 bends upward or downward on the plane of paper, it is not possible to identify a direction in which an external force Fy applied in the Y direction acts between positive and negative directions (upward and downward directions on the plane of paper).

On the other hand, in a case where a pair of detecting elements 321 and 322 is attached to the cantilever 301 in the Y direction as illustrated in FIG. 3(B), when the cantilever 301 bends upward on the plane of paper, one distortion detecting element 321 compresses and the other distortion detecting element 322 extends, and in contrast, when the cantilever 301 bends downward on the plane of paper, one distortion detecting element 321 extends and the other distortion detecting element 322 compresses. Therefore, by attaching the pair of detecting elements 321 and 322 in the Y direction, it becomes possible to identify the direction in which the external force Fy applied in the Y direction acts.

Therefore, as illustrated in FIG. 2, by attaching the pair of distortion detecting elements 201 and 202 to the first blade 111, it becomes possible to detect the external forces in the two directions of the Z direction and the Y direction acting on the first blade 111.

Similarly, the second blade 112 may be considered as a cantilever having the forceps rotational axis 113 as a fixed end. Therefore, a pair of distortion detecting elements including a distortion detecting element 203 for detecting distortion on an inner side of an opening/closing structure and a distortion detecting element 204 for detecting distortion on an outer side of the opening/closing structure of the second blade 112 as a distortion generating body is attached to the second blade 112 so that external forces in the two directions of the Z direction and the Y direction acting on the second blade 112 may be detected.

It is possible to calculate the external force Fz in the Z direction acting on the forceps unit 110 as the end effector of the surgical system 100 and a total gripping force Fg acting from a gripping target (not illustrated) on the first blade 111 and the second blade 112 when the forceps unit 110 is subjected to the opening/closing operation by performing an arithmetic process of detection signals of the pair of distortion detecting elements 201 and 202 attached to the first blade 111 and the pair of distortion detecting elements 203 and 204 attached to the second blade 112 by a signal processing unit (not illustrated in FIG. 2). The arithmetic process by the signal processing unit is described later in detail. It may also be said that a sensor having two degrees of freedom (2 DOF) is configured to detect the acting force Fz on the forceps unit 110 including the first blade 111 and the second blade 112 and the total gripping force Fg.

In order to measure the force acting on the end effector 110 without an influence by noise due to vibration or inertia, it is desirable to arrange a force sensor as close as possible to a tip end. It should be understood that the configuration of the distortion detecting elements 201 to 204 as illustrated in FIG. 2 also meets this need.

It is more preferable that the first blade 111 and the second blade 112 are structure bodies having not a simple blade shape but an easily deformed shape from a viewpoint of being used as the distortion generating body. For example, when a hole or a notch is formed in the simple blade shape, stress (internal force per unit area generated on a cross-section of an object) tends to be concentrated when the external force is applied, and as a result, this tends to be deformed and performance as the distortion generating body is improved.

A specific configuration example of the first blade 111 in which the distortion generating body is formed is described with reference to FIG. 4. FIG. 4(A) illustrates a side surface (YZ plane) to which the distortion detecting elements 201 and 202 are attached and FIG. 4(B) illustrates a XZ cross-section of the first blade 111 in a part of which a distortion generating body 401 is formed. The distortion generating body 401 having a meander structure is formed on a part of the first blade 111. The first blade 111 easily compresses and extends against the external forces acting in the Z direction and the X direction by the presence of the distortion generating body 401 having the meander structure in which folding or meandering is repeated on the ZX plane as illustrated. In other words, it may be said that the distortion generating body is formed in at least a part of the first blade 111.

Figure 4:
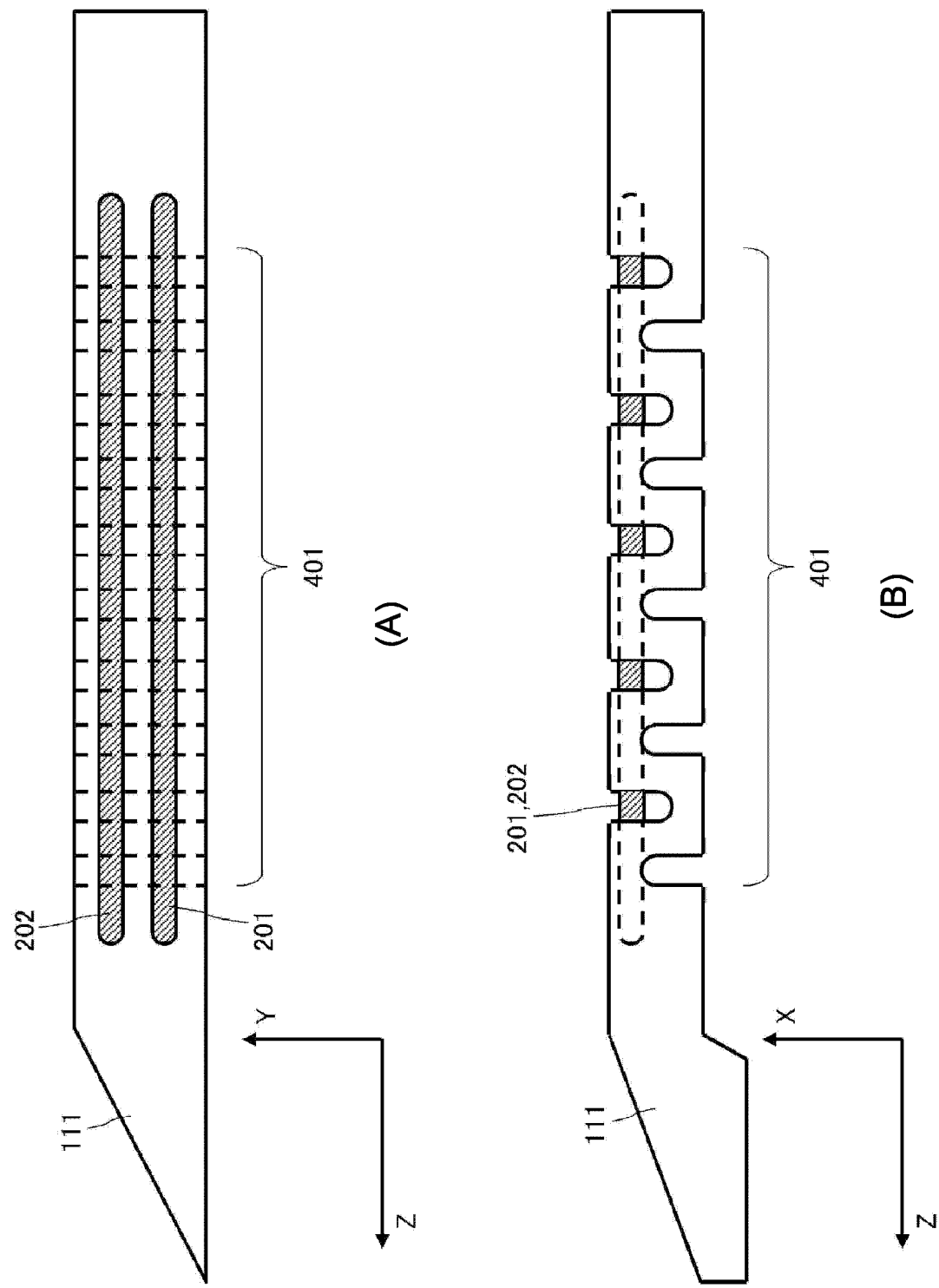
FIG. 4 is a view illustrating a configuration example of a first blade 111 in which a distortion generating body having a meander structure is configured.

As illustrated in FIG. 4, by attaching the distortion detecting elements 201 and 202 to the portion of the distortion generating body 401 in the first blade 111, it becomes easy to detect the force acting on the first blade 111. Note that, although not illustrated, it should be understood that the distortion generating body of the meander structure having a shape symmetrical to the first blade 111 is similarly formed on the second blade 112. However, the distortion generating bodies formed on the first blade 111 and the second blade 112 are not especially limited to have the meander structure, and may have various other shapes in which the stress is easily concentrated which may be used as the distortion generating body.

The first blade 111 and the second blade 112 are manufactured by using, for example, stainless steel (steel use stainless: SUS), a Co—Cr alloy, or a titanium-based material known as a metal-based material having excellent biocompatibility. From a viewpoint of forming the distortion generating body 401 in a part of the structure as described above, the first blade 111 and the second blade 112 are preferably manufactured by using a material having a mechanical characteristic such as high strength and low rigidity (low Young's modulus), for example, a titanium alloy. By using a low-rigidity material for the distortion generating body, it becomes possible to measure the acting force with high sensitivity.

In short, the end effector 110 as the elongated tube part having a configuration in which at least one distortion generating body and one distortion detecting element are arranged between the distal end and a proximal end may measure a force in one or more axes acting on the end effector. Furthermore, although the pulling force required for gripping by the forceps unit 110 is transmitted by the cable (as described above), when measuring the force acting on the first blade 111 and the second blade 112 from the first blade 111 and the second blade 112 themselves configured as the distortion generating bodies, they do not interfere with the pulling force of the cable. Especially, it is possible to measure with high sensitivity the force Fz acting in the long axis direction of the forceps unit 110 as the end effector. In addition, there also is an effect of reducing mechanical vibration noise by reducing real inertia on a subsequent stage of the sensor that uses the first blade 111 and the second blade 112 as the distortion generating body.

As the distortion detecting element, a capacitance type sensor, a semiconductor distortion gauge, a foil distortion gauge and the like are also widely known in this field, and any one of them may be used as each of the distortion detecting elements 201 to 204 which measure the distortion of the first blade 111 and the second blade 112. However, in this embodiment, a fiber bragg grating (FBG) sensor manufactured using an optical fiber is used as the distortion detecting elements 201 to 204.

Here, the FBG sensor is a sensor configured by engraving a diffraction grating (grating) along a long axis of the optical fiber, which may detect change in interval of the diffraction grating due to the distortion generated by the acting force and the extension or compression associated with change in temperature as change in wavelength of reflected light with respect to incident light of a predetermined wavelength band (Bragg wavelength) (well known). Then, the change in wavelength detected from the FBG sensor may be converted into the distortion, stress, and change in temperature which become a cause.

In this embodiment, it is assumed that the signal processing unit which processes the detection signals is arranged in a place apart from the forceps unit 110 to which the distortion detecting elements 201 to 204 are attached. Since the FBG sensor using the optical fiber has a small transmission loss (a noise from the outside hardly superposes), detection accuracy may be maintained with high accuracy even under an assumed usage environment. Furthermore, the FBG sensor also has an advantage that sterilization handling and handling under high magnetic field environment necessary for medical treatment are easy.

A method of installing the distortion detecting elements 201 and 202 using the FBG sensors on the first blade 111 is described with reference to FIGS. 5 and 6. Although the second blade 112 is not illustrated, it should be understood that this is similar to that in FIGS. 5 and 6.

Figure 5:
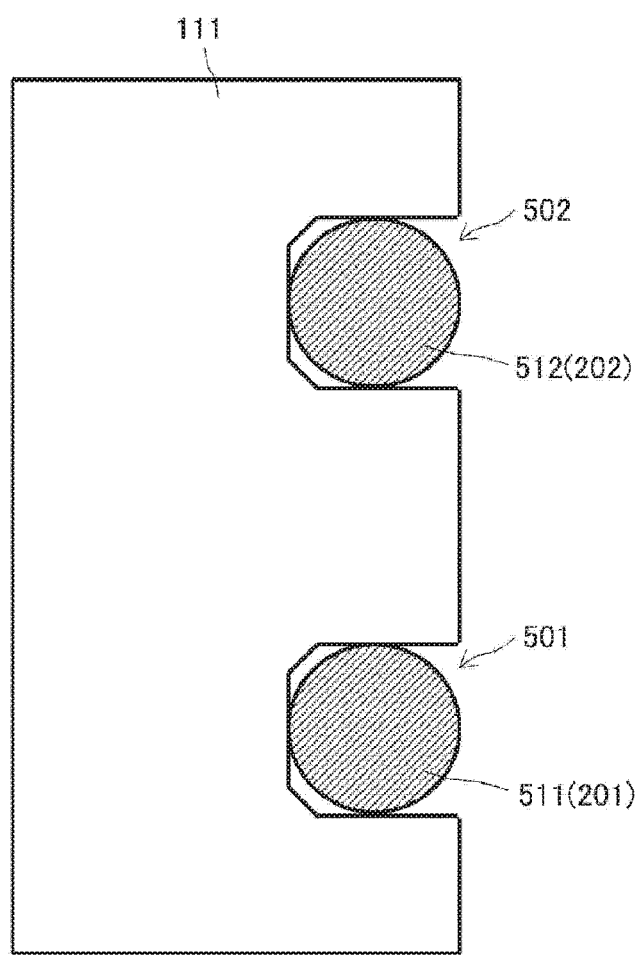
FIG. 5 is a view for explaining a method of installing distortion detecting elements 201 and 202 using FBG sensors on the first blade 111.

FIG. 5 illustrates an XY cross-section of the first blade 111. On a surface of the first blade 111, two grooves 501 and 502 are engraved in the long axis direction (Z direction). Then, optical fibers 511 and 512 are attached to the inner side and the outer side of the first blade 111 by being embedded in the grooves 501 and 502, respectively, so that an outline of the first blade 111 does not swell. The optical fibers 511 and 512 are fixed to the surface of the first blade 111 with an adhesive or the like at several locations (to be described later). Therefore, when the external force acts to deform the first blade 111, the optical fibers 511 and 512 deform integrally with the first blade 111.

Locations where the diffraction grating is engraved out of the attached optical fibers 511 and 512 act as the FBG sensors. Therefore, the diffraction gratings are engraved in ranges overlapping with the distortion generating bodies (described above) out of the optical fibers 511 and 512 laid in the long axis direction of the first blade 111 to form the FBG sensors to be used as the distortion detecting elements 201 and 202 for detecting the distortion on the inner side and the outer side of the first blade 111.

Furthermore, FIG. 6(A) illustrates the side surface (YZ plane) on which the above-described grooves 501 and 502 are engraved and FIG. 6(B) illustrates the XZ cross-section of the optical fibers 511 and 512 are embedded in first blade 111. The two grooves 501 and 502 engraved in the long axis direction (Z direction) of the surface of the first blade 111. The diffraction gratings are engraved in the ranges overlapping with the distortion generating bodies 401 out of the optical fibers 511 and 512 to form the FBG sensors to be used as the distortion detecting elements 201 and 202. Portions where the FBG sensors include the optical fibers 511 and 512 are shaded in the drawing.

Furthermore, the optical fibers 511 and 512 are fixed to the surface of the first blade 111 with an adhesive or the like at both ends 601 to 604 of the portions where the FBG sensors are formed. Therefore, when the external force acts to deform the portion of the distortion generating body 401 of the first blade 111, the optical fibers 511 and 512 also integrally deform, and the distortion is generated in the FBG sensor portions, in other words, the distortion detecting elements 201 and 202.

Figure 6:
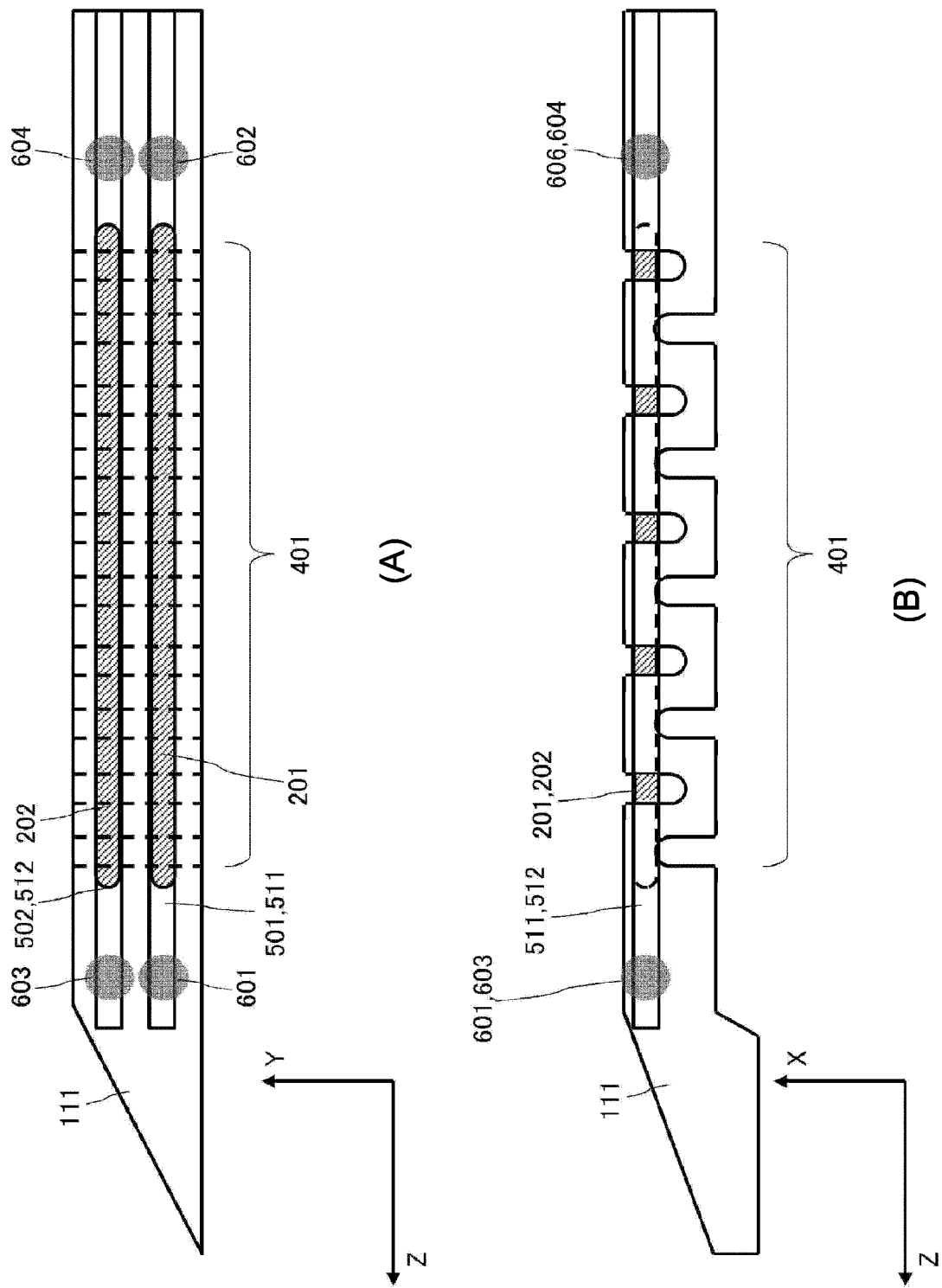
FIG. 6 is a view for explaining a method of installing the distortion detecting elements 201 and 202 using the FBG sensors on the first blade 111.

As is understood from FIG. 6, the optical fibers 511 and 512 are fixed at two locations near the tip end and a base of the first blade 111. Therefore, since the distortion generated between these two fixed points may be detected by the distortion detecting elements 201 and 202 formed by using the FBG sensors, the force acting in a wide range from the tip end to the base of the first blade 111 may be detected.

Note that, in FIG. 6, only a part of the optical fibers forming the FBG sensors used as the distortion detecting elements 201 and 202 (part where the distortion generating body of the first blade 111 is formed) is illustrated, and the other parts is not illustrated. It should be understood that the other end of the optical fiber not illustrated actually extends beyond the forceps rotational axis 113 to a detecting unit and the signal processing unit (neither is illustrated).

Although the second blade 112 is not illustrated, as is the case with the first blade 111, the distortion detecting elements 203 and 204 formed by the FBG sensors using two optical fibers embedded in the grooves engraved on the side surface of the second blade 112 may be formed on the inner side and outer side of the second blade 112. In short, four optical fibers are laid in the entire forceps unit 110.

Furthermore, an FBG sensor to be compared with the distortion detecting elements 201 and 202 (hereinafter, referred to as "dummy FBG sensor") may be formed in a portion separated from the distortion generating bodies of the first blade 111 and the second blade 112 out of the optical fibers attached as the distortion detecting elements 201 and 202. On the basis of a detection result of the dummy FBG sensor, it is possible to detect a wavelength change $\Delta\lambda_{temp}$ caused by the temperature change, and furthermore, it is possible to use the same in a temperature compensating process on the detection results of the distortion detecting elements 201 and 202.

Figure 7:
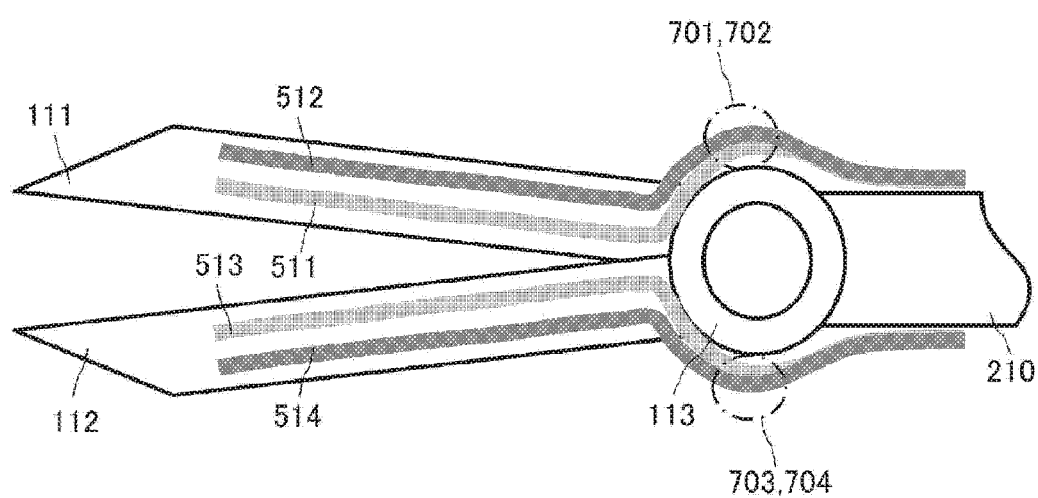
FIG. 7 is a view illustrating an example in which a part of optical fibers forming the distortion detecting elements 201 and 202 is used as dummy FBG sensors 701 to 704.

FIG. 7 illustrates an example in which the dummy FBG sensors are arranged on the optical fibers 511 to 514 attached to the forceps unit 110. As described above, the FBG sensors as the distortion detecting elements 201 to 204 are formed in the locations laid on the first blade 111 and the second blade 112 out of the optical fibers 511 to 514. Moreover, diffraction gratings are engraved at portions straddling the forceps rotational axis 113 indicated by reference numerals 701 to 704 out of the optical fibers 511 to 514 and the dummy FBG sensor is formed on each of the portions. As is understood from the drawing, the dummy FBG sensors 701 to 704 are formed in portions not attached to the first blade 111 or the second blade 112 out of the optical fibers 511 to 514 (in other words, portions not fixed to the distortion generating body). Therefore, it is possible to estimate that the wavelength change detected by each of the dummy FBG sensors 701 to 704 is the wavelength change caused only by the temperature change not affected by the distortion of the first blade 111 or the second blade 112.

The detecting unit and the signal processing unit are arranged at a location apart from the end effector, for example, near the base of the surgical system 100. A total length of the optical fibers 511 to 514 is assumed to be about 400 mm. The detecting unit allows light of a predetermined wavelength (Bragg wavelength) to be incident on the optical fibers 511, 512, . . . attached to the first blade 111 and the second blade 112, and receives the reflected light thereof to detect a wavelength change $\Delta\lambda$ in the FBG sensor portion. Then, the signal processing unit converts the detected wavelength change $\Delta\lambda$ into a force F acting on the distortion generating body.

Furthermore, the signal processing unit may also compensate for the wavelength change due to the temperature change by using the signal component detected from the above-described dummy FBG sensor at the time of this calculation (a method of performing the temperature compensation using the distortion component detected by the dummy sensor is also known in this field as a two-gauge method using two distortion gauges, for example). A processing method (algorithm) for converting the wavelength change $\Delta\lambda$ into a force is described later in detail.

With reference to FIG. 2 again, the rear end of the forceps unit 110 is coupled to the first link 210 via the joint that defines the forceps rotational axis 113. It may also be said that the forceps unit 110 is attached to the tip end of the first link 210.

The first link 210 may be regarded as a cantilever having a first joint axis 220 as a fixed end. On an outer periphery of the first link 210, a plurality of distortion detecting elements for detecting distortion in the XY directions at two different positions a and b in the long axis direction is attached. Specifically, at the position a, a pair of distortion detecting elements 211a and 213a (not illustrated) for detecting the distortion amount in the X direction of the first link 210 is attached to opposite sides, and a pair of distortion detecting elements 212a and 214a for detecting the distortion amount in the Y direction is attached to opposite sides. Similarly, at position b, a pair of distortion detecting elements 211b and 213b (not illustrated) for detecting the distortion amount in the X direction of the first link 210 is attached, and a pair of distortion detecting elements 212b and 214b for detecting the distortion amount in the Y direction is attached.

In this manner, it is configured such that the distortion amounts in the XY directions may be detected at the two different positions a and b in the long axis direction of the first link 210. Although a translational force may be calculated from the distortion amount at one position of the cantilever, moment cannot be calculated. On the other hand, it is an obvious matter in structural mechanics that the moment as well as the translational force may be calculated from the distortion amounts at two or more positions. According to the configuration illustrated in FIG. 2, the translational forces Fx and Fy in the two directions and moments Mx and My in two directions acting on the first link 210 may be calculated on the basis of the distortion amounts in the XY directions detected at the two positions a and b.

Therefore, it may also be said that a sensor having 4 DOF is formed in the first link 210. This 4 DOF sensor may measure the translational forces Fx and Fy in the two directions and the moments Mx and My in the two directions acting on the end effector 110 by utilizing the fact that the first link 210 is deformed by the external force acting on the end effector 210.

The external force Fy acting in the Y direction (vertical direction on the plane of paper) orthogonal to the long axis direction (Z direction) cannot be separated from the total gripping force Fg acting when closing the first blade 111 and the second blade 112 to grip the gripping target only with the 2 DOF sensor formed on the forceps unit 110. Therefore, the translational force Fy in the Y direction is detected using the 4 DOF sensor formed on the first link 210.

Figure 8:
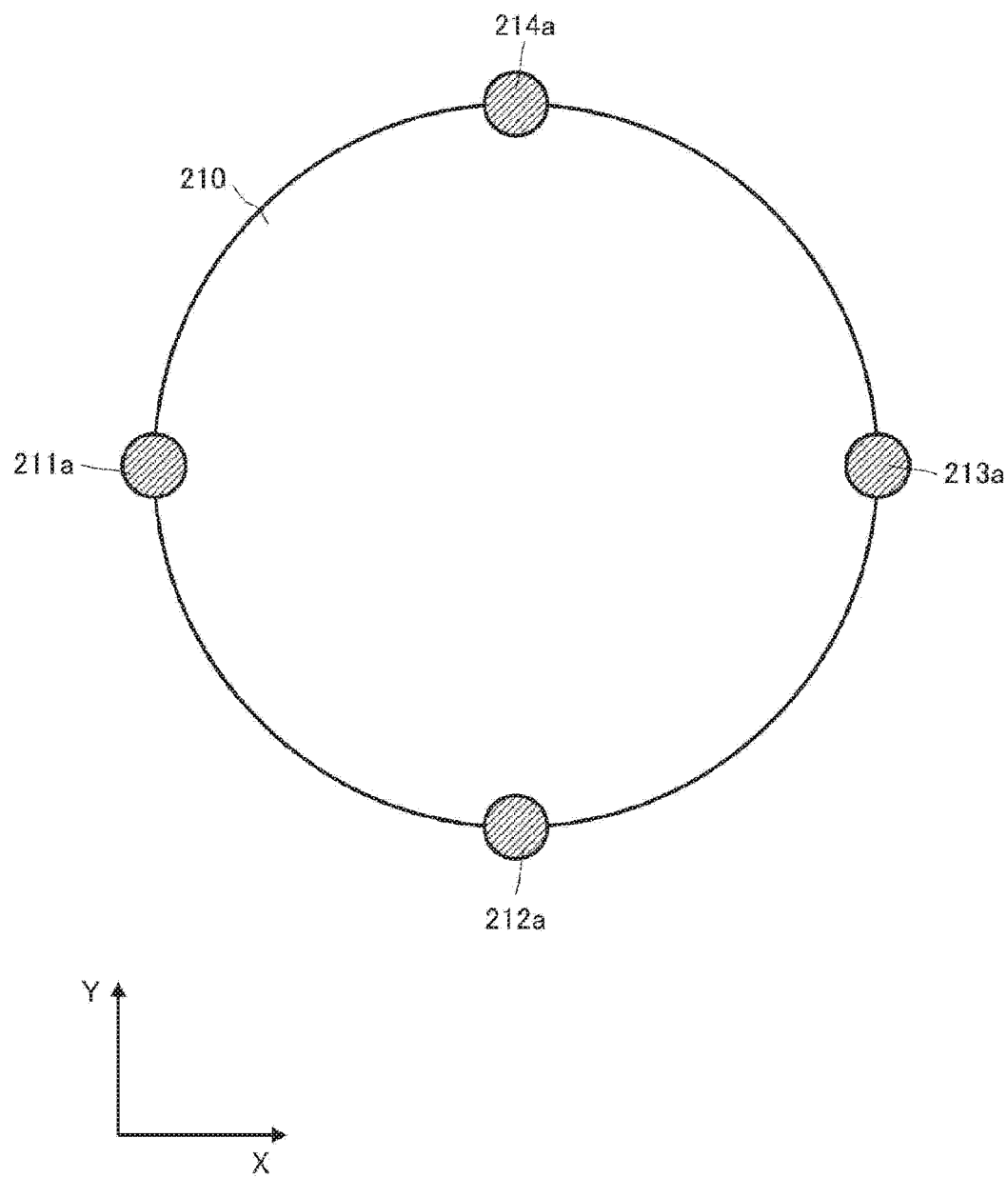
FIG. 8 is a view illustrating an XY cross-section of a first link 210 to which distortion detecting elements 211a to 214a are attached.

FIG. 8 illustrates an XY cross-section at the position a of the first link 210. As is understood from the drawing, the pair of distortion detecting elements 211a and 213a for detecting the distortion amount in the X direction is attached to the opposite sides in the X direction of the outer periphery of the first link 210, and the pair of distortion detecting elements 212a and 214a for detecting the distortion amount in the Y direction is attached to the opposite sides in the Y direction of the outer periphery of the first link 210. Note that, although not illustrated, similar to FIG. 8, on the XY cross-section at the position b of the first link 210, the pair of distortion detecting elements 211b and 213b for detecting the distortion amount in the X direction is attached to the opposite sides in the X direction of the outer periphery of the first link 210, and the pair of distortion detecting elements 212b and 214b for detecting the distortion amount in the Y direction is attached to the opposite sides in the Y direction of the outer periphery of the first link 210.

By taking a difference in detection signal between the distortion detecting elements 211a and 213a on the opposite sides, it is possible to cancel the component caused by the temperature change and perform temperature compensation. Specifically, the distortion amount detected by each of the distortion detecting elements 211a and 213a includes a distortion component caused by the external force and a distortion component due to expansion of the first link 210 as the distortion generating body accompanying with an increase in temperature. Here, since the latter distortion components due to the expansion on the opposite sides coincide, it is possible to cancel the distortion component caused by the temperature change by taking the difference between the detection results of the distortion detecting elements 211a and 213a, and extract only the distortion amount caused by the external force.

A method of performing temperature compensation by taking the difference in detection value between the sensors installed on the opposite sides is also known in this field also as a four-gauge method using, for example, four distortion gauges.

Similarly, the pair of distortion detecting elements 212a and 214a for detecting the distortion amount in the Y direction is attached to the opposite sides in the Y direction of the first link 210, and it is possible to cancel the component caused by the change in temperature by taking the difference in detection signal between the distortion detecting elements 212a and 214a on the opposite sides to perform the temperature compensation.

Note that, although not illustrated, the pair of distortion detecting elements 211b and 213b is attached to the opposite sides in the X direction and the pair of distortion detecting elements 212b and 214b are attached on the opposite sides in the Y direction for the temperature compensation also on the outer periphery of the position b of the first link 210.

In FIG. 2 and FIG. 8, the first link 210 is illustrated as a simple cylindrical shape in order to simplify the drawing. When the first link 210 is formed into a shape easily deformed by stress concentrating at each of two measurement positions a and b in the long axis direction, the distortion amounts are easily measured in the distortion detecting elements 211a to 214a and 211b to 214b, and it is expected that a performance of detection as the 4 DOF sensor is improved.

Furthermore, in this embodiment, the FBG sensors using the optical fibers are used as the distortion detecting elements 211a to 214a and 211b to 214b. It goes without saying that it is also conceivable to use other types of distortion detecting elements widely known in this field such as capacitive sensors, semiconductor distortion gauges and foil distortion gauges as a variation. However, the FBG sensor is considered to be more preferable in consideration of the advantages such as small transmission loss, and the sterilization handling and the handling under the high magnetic field environment necessary for the medical treatment (as described above).

A structure of the first link 210 configured to be easily deformed at the two measurement positions a and b, and a method of installing the distortion detecting elements 211a to 214a and 211b to 214b using the FBG sensor on the first link 210 are described with reference to FIG. 9.

FIG. 9(A) illustrates a YZ cross-section and FIG. 9(B) illustrates a ZX cross-section of the first link 210. In the drawing, portions of the YZ cross-section and the ZX cross-section of the first link 210 are filled with gray. It should be understood that the first link 210 has a shape rotationally symmetrical around the long axis.

As illustrated, the first link 210 has a necked structure having concave portions at which a radius is gradually reduced at the two different measurement positions a and b in the long axis direction. Therefore, when a force acts in at least one of the XY directions, the first link 210 tends to be deformed due to the stress concentration at each of the measurement positions a and b. The first link 210 is preferably manufactured using a titanium alloy which is high in strength and low in rigidity as compared to a steel material such as SUS or iron steel as a material.

On the outer periphery of the first link 210, a pair of optical fibers 902 and 904 are laid in the long axis direction on the opposite sides in the Y direction. Similarly, on the outer periphery of the first link 201, a pair of optical fibers 901 and 903 are laid in the long axis direction on the opposite sides in the X direction. In short, four optical fibers 901 to 904 are laid in the entire first link 210.

Note that, together with the optical fibers 511 to 514 laid in the forceps unit 110, eight optical fibers are used in the entire surgical system 100. However, a configuration example may be considered in which four optical fibers are used by multiplexing the optical fibers of the forceps unit 110 and the optical fibers of the first link 210.

Out of the optical fibers 902 and 904 laid on the opposite sides in the Y direction, the FBG sensors are formed by engraving the diffraction gratings in the ranges overlapping with the two recessed portions of the first link 201 (or near the measurement positions a and b) to be used as the distortion detecting elements 212a, 212b, 214a, and 214b. Portions of the optical fibers 902 and 904 where the FBG sensors are formed are shaded in the drawing.

Furthermore, the optical fibers 902 and 904 are fixed to the surface of the first link 210 with an adhesive or the like at both ends 911 to 913 and 914 to 916 of the portions where the FBG sensors are formed. Therefore, when the external force acts and the first link 210 bends in the Y direction, the optical fibers 902 and 904 also integrally deform, and the distortion occurs in the FBG sensor portions, tin other words, the distortion detecting elements 212a, 212b, 214a, and 214b.

Similarly, out of the optical fibers 901 and 903 laid on the opposite sides in the X direction, the FBG sensors are formed by engraving the diffraction gratings in the ranges overlapping with the two recessed portions of the first link 201 (or near the measurement positions a and b) to be used as the distortion detecting elements 211a, 211b, 213a, and 213b. Portions of the optical fibers 901 and 903 where the FBG sensors are formed are shaded in the drawing.

Furthermore, the optical fibers 901 and 903 are fixed to the surface of the first link 210 with an adhesive or the like at both ends 921 to 923 and 924 to 926 of the portions where the FBG sensors are formed. Therefore, when the external force acts and the first link 210 bends in the X direction, the optical fibers 901 and 903 also integrally deform, and the distortion occurs in the FBG sensor portions, in other words, the distortion detecting elements 211a, 211b, 213a, and 213b.

Figure 9:
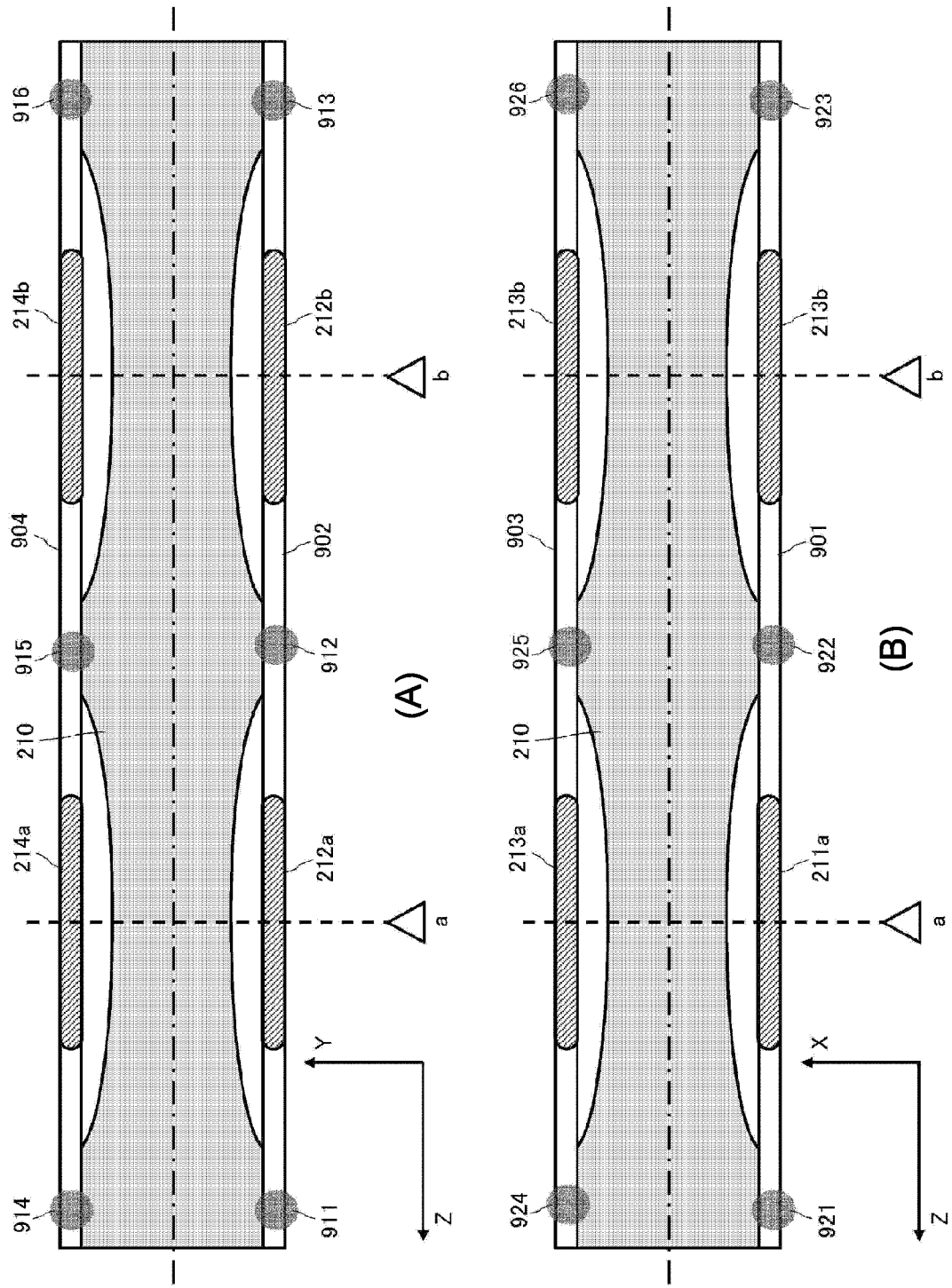
FIG. 9 is a view for explaining a method of installing the distortion detecting elements 211a to 214a and 211b to 214b using the FBG sensors on the first link 210.

In FIG. 9, only the portion attached to the outer periphery of the first link 210 is drawn out of the optical fibers 901 to 904 used as the distortion detecting elements 211a to 214a and 211b to 214b, and the other portions are not illustrated. It should be understood that the other ends of the optical fibers 901 to 904 actually extend beyond the first joint 221 to the detecting unit and the signal processing unit (neither is illustrated). A total length of the optical fibers 901 to 904 is assumed to be about 400 mm, for example.

The detecting unit and the signal processing unit are arranged at a location apart from the end effector, for example, near the base of the surgical system 100. The detecting unit allows light of a predetermined wavelength (Bragg wavelength) to be incident on the optical fibers 901 to 904 and receives the reflected light thereof to detect a wavelength change $\Delta\lambda$. Then, the signal processing unit calculates the translational forces Fx and Fy in the two directions and the moments Mx and My in the two directions acting on the end effector 110 on the basis of the wavelength change detected from each of the FBG sensors as the distortion detecting elements 211a to 214a and 211b to 214b attached to the opposite sides in the XY directions of the first link 210 so as to be opposed. The arithmetic process by the signal processing unit is described later in detail.

Note that, in this specification, although the 4 DOF sensor formed on the first link 210 the closest to the end effector 110 is described as one of the best embodiments, another embodiment of forming the 4 DOF sensor on another link of the articulated arm 120 at the tip end of which the end effector 110 is attached such as a second link is also conceivable.

Furthermore, as illustrated in FIG. 9, since the structure is such that distortion detecting element is not directly attached to the surface of the distortion generating body, but indirectly attached via the optical fiber, transmission of heat of the distortion generating body to the element is inhibited, and there is an effect that the detection accuracy of the distortion detecting element is improved.

A reason that this effect occurs is described. When the capacitive sensor, semiconductor distortion gauge, foil distortion gauge, or the like known as the distortion detecting element is arranged in close contact with the distortion generating body, the heat of the distortion generating body is transmitted to the distortion detecting element to generate detection noise. Furthermore, the semiconductor distortion gauge and foil distortion gauge have a problem of self-heating, and in a case where they are in direct contact with the distortion generating body, they affect a temperature characteristic of the distortion generating body and distortion detecting element, and the detection accuracy is deteriorated. Therefore, with the structure in which the distortion detecting element is attached via the optical fiber having thermal conductivity lower than that of the distortion generating body, the heat of the distortion generating body is inhibited from being transmitted to the distortion detecting element, and the detection accuracy of the distortion detecting element may be improved.

The structure of the surgical system 100 according to this embodiment is mainly described heretofore. Subsequently, a processing algorithm implemented by the signal processing unit for calculating the force acting on the end effector (forceps unit 110) on the basis of the detection signals of the 2 DOF sensor formed in the forceps unit 110 and the 4 DOF sensor formed in the first link 210 is described.

Figure 10:
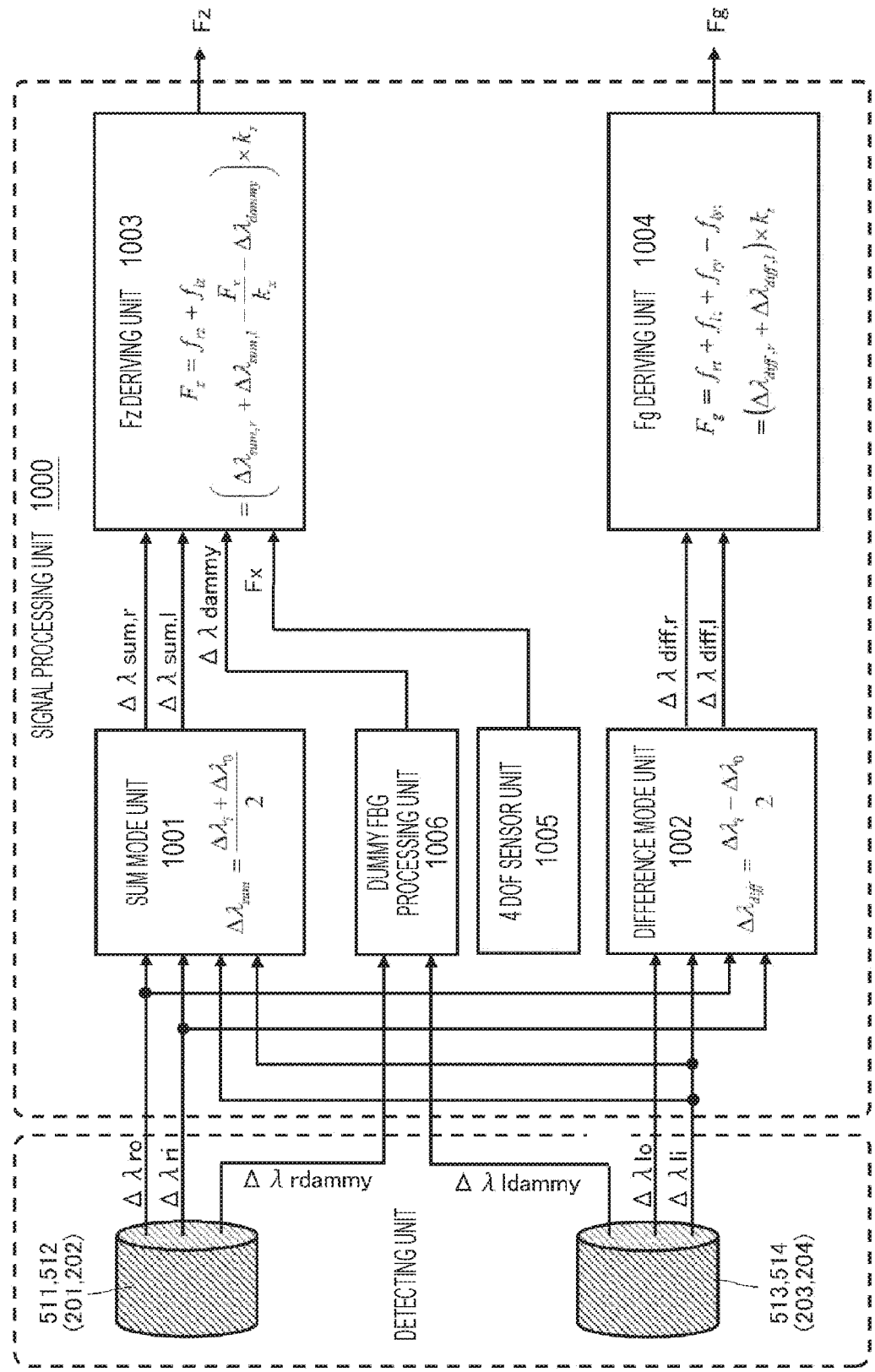
FIG. 10 is a view for explaining an algorithm of an arithmetic process performed by a signal processing unit 1000.

FIG. 10 schematically illustrates the processing algorithm for the 2 DOF sensor for calculating the force Fz acting in the long axis direction of the forceps unit 110 as the end effector and the total gripping force Fg in the forceps unit 110 on the basis of the detection results obtained from the FBG sensor formed on each of the optical fibers 511 and 512 laid on the first blade 111 and the optical fibers 513 and 514 laid on the second blade 112 in a signal processing unit 1000.

Figure 11:
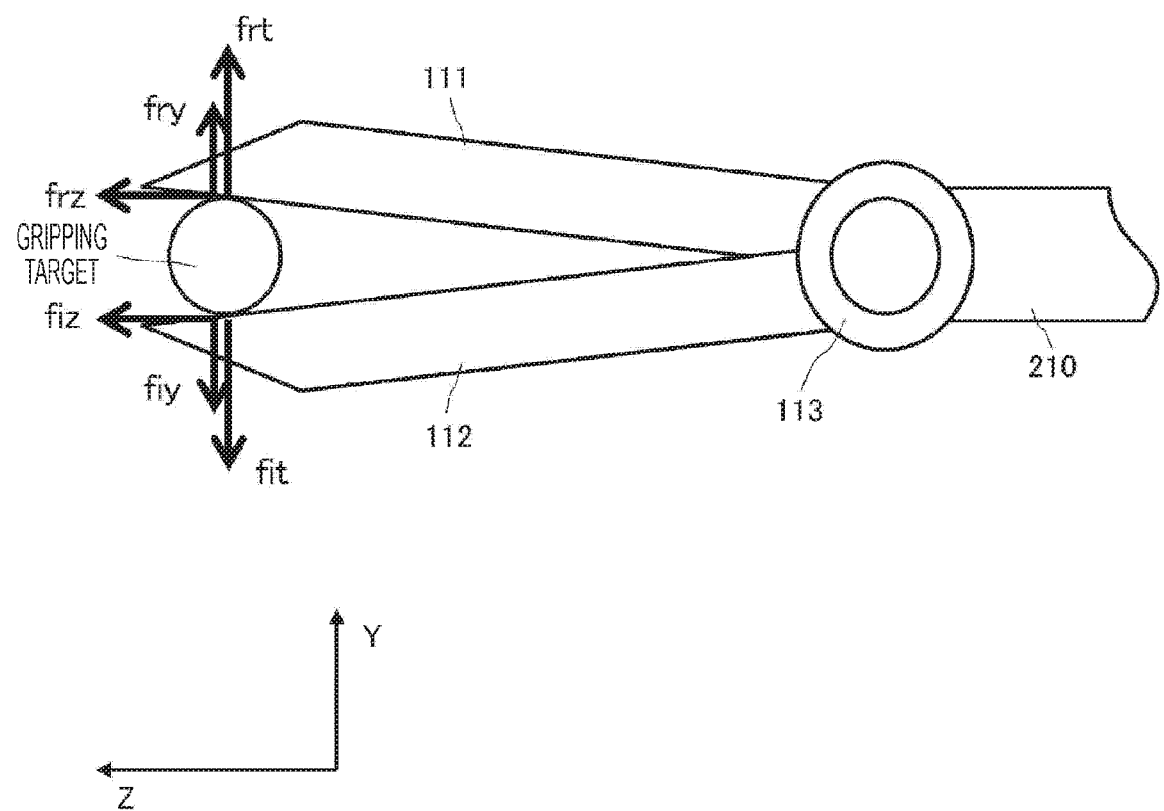
FIG. 11 is a view illustrating external forces in YZ directions acting on the first blade 111 and the second blade 112 and an acting force from a gripping target.

The external forces Fx, Fy, and Fz in the XYZ directions, respectively, act on the first blade 111 and the second blade 112 forming the forceps unit 110 as the end effector. Furthermore, when the forceps unit 110 closes and grips the target, a force Ft from the gripping target acts on the first blade 111 and the second blade 112. As illustrated in FIG. 11, the external forces in the YZ directions and acting force from the gripping target acting on the first blade 111 are defined as fry, frz, and frt, respectively, and the external forces in the YZ directions and acting force from the gripping target acting on the second blade 112 are defined as fly, flz, and flt, respectively.

Figure 12:
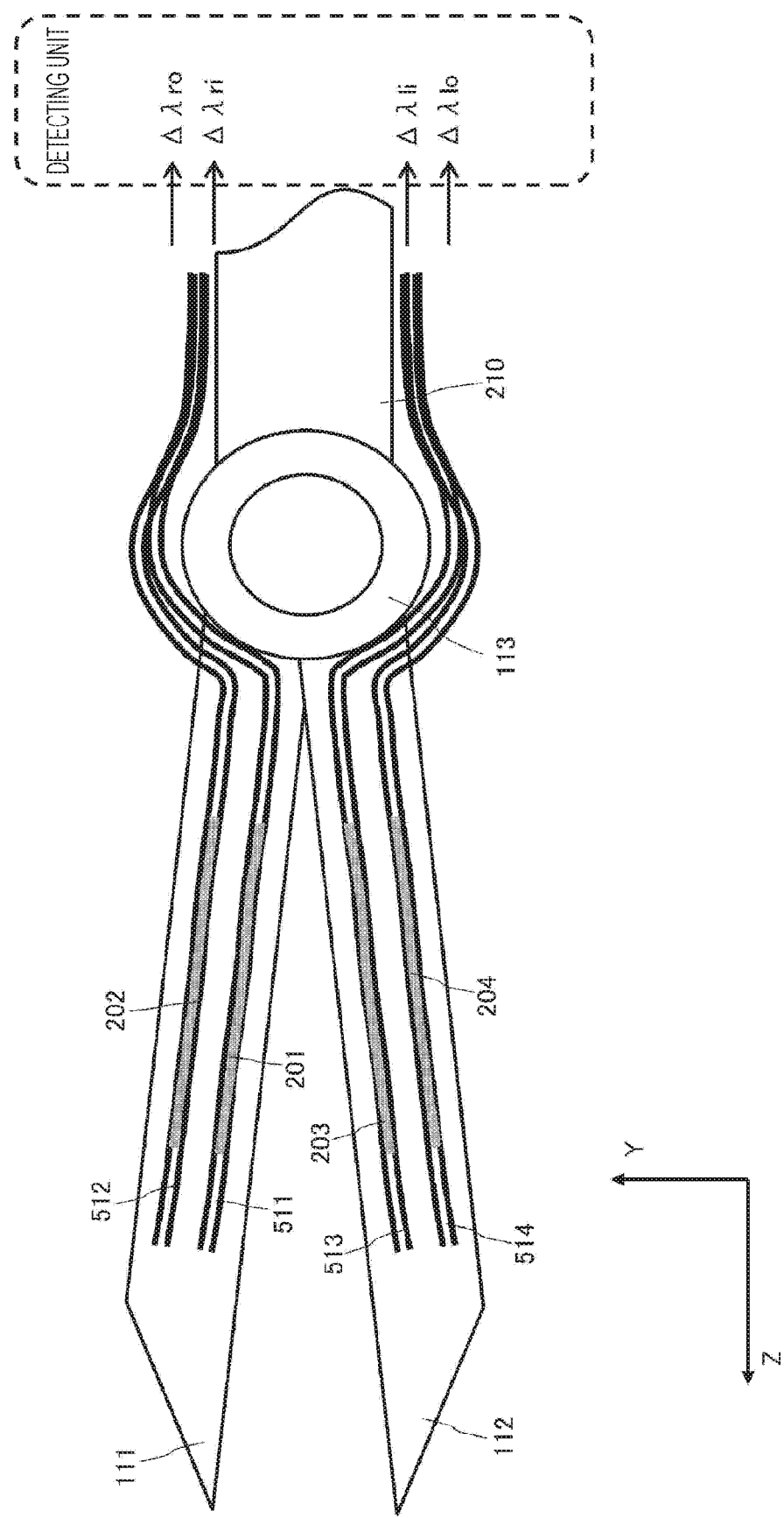
FIG. 12 is a view for explaining an algorithm of an arithmetic process performed by a signal processing unit.

FIG. 12 illustrates a state in which the wavelength change of each FBG sensor on the optical fibers 511 to 514 attached to the first blade 111 and the second blade 112 is detected by the detecting unit.

The detecting unit detects wavelength changes $\Delta\lambda$ri and $\Delta\lambda$ro in the FBG sensors as the distortion detecting elements 201 and 202 arranged on the inner side and the outer side of the first blade 111, respectively, on the basis of the reflected light of the incident light of a predetermined wavelength band to the optical fibers 511 and 512. The wavelength changes $\Delta\lambda$ri and $\Delta\lambda$ro include wavelength change components caused by the external forces Fx, Fy, and Fz and the acting force Ft from the gripping target, and the wavelength change component caused by the temperature change.

Furthermore, the detecting unit receives the reflected light of the incident light of a predetermined wavelength band to the optical fibers 513 and 514 and detects wavelength changes $\Delta\lambda$li and $\Delta\lambda$lo in the FBG sensors as the distortion detecting elements 203 and 204 arranged on the inner side and the outer side of the second blade 112, respectively. The wavelength changes $\Delta\lambda$li and $\Delta\lambda$lo include the wavelength change components caused by the external forces Fx, Fy, and Fz and the acting force Ft from the gripping target, and the wavelength change component caused by the temperature change. In the following, it is supposed that the components caused by the temperature change included in the wavelength changes $\Delta\lambda$ri and $\Delta\lambda$li of the optical fibers 511 and 513 being the opposite sides are equal, and the components caused by the temperature change included in the wavelength changes $\Delta\lambda$ro and $\Delta\lambda$lo of the optical fibers 512 and 514 being the opposite sides are equal.

Furthermore, although not illustrated in FIG. 12, the detecting unit detects the wavelength change in the dummy FBG sensor provided in each of the optical fibers 511 to 514. The signal processing unit on the latter stage uses the sum of the detection values of the four dummy FBG sensors or a value obtained by multiplying the total value by a calibration gain as a wavelength change amount $\Delta\lambda_{dummy}$ of the dummy FBG sensor (described later). The wavelength change amount $\Delta\lambda_{dummy}$ is a wavelength change component caused by the temperature change in each of the optical fibers 511 to 514.

Here, the wavelength changes $\Delta\lambda$ri and $\Delta\lambda$ro detected by the detecting unit from the optical fibers 511 and 512, respectively, are equivalent to an inner distortion amount $\Delta\varepsilon$ri and an outer distortion amount $\Delta\varepsilon$ro generated on the inner side and the outer side of the first blade 111 when the force acts on the first blade 111 (in a case where the component of the wavelength change caused by the temperature change is ignored). Furthermore, the wavelength changes $\Delta\lambda$li and $\Delta\lambda$lo detected by the detecting unit from the optical fibers 513 and 514, respectively, are equivalent to an inner distortion amount $\Delta\varepsilon$li and an outer distortion amount $\Delta\varepsilon$lo generated on the inner side and the outer side of the second blade 112 when the force acts on the second blade 112 (in a case where the component of the wavelength change caused by the temperature change is ignored).

It may also be said that the external forces Fx, Fy, and Fz and the acting force Ft from the gripping object are inputs to the end effector 110, and the inner distortion amount $\Delta\varepsilon$ri and the outer distortion amount $\Delta\varepsilon$ro of the first blade 111 and the inner distortion amount $\Delta\varepsilon$li and the outer distortion amount $\Delta\varepsilon$lo of the second blade 112 are outputs from the end effector 110. A relationship of distortion directions of the distortion amounts $\Delta\varepsilon$ when each of the acting forces Fx, Fy, Fz, and Ft acts in a positive direction is illustrated in following Table 1. In the table, + indicates extension and − indicates compression.

TABLE 1

| | FIRST FORCEPS UNIT | | SECOND FORCEPS UNIT | |
|---|---|---|---|---|
| INPUT | INNER DISTORTION $\Delta\varepsilon$ri | OUTER DISTORTION $\Delta\varepsilon$ro | INNER DISTORTION $\Delta\varepsilon$li | OUTER DISTORTION $\Delta\varepsilon$lo |
| Fx | + | + | + | + |
| Fy | + | − | − | + |
| Fz | + | + | + | + |
| Ft | + | − | + | − |

It is understood from Table 1 that the inner distortion $\Delta\varepsilon$ri and the outer distortion $\Delta\varepsilon$ro generated in the first blade 111 when the external forces Fx and Fz in the X direction and the Z direction act have the same sign. Therefore, it is possible to extract a distortion amount component caused by the force Fx acting in the X direction and the force Fz acting in the Z direction on the forceps unit 110 by taking the sum of the inner distortion $\Delta\varepsilon$ri and the outer distortion $\Delta\varepsilon$ro generated in the first blade 111 and the sum of the inner distortion $\Delta\varepsilon$li and the outer distortion $\Delta\varepsilon$lo generated in the second blade 112.

On the other hand, it is understood that, the inner distortion $\Delta\varepsilon$ri and the outer distortion $\Delta\varepsilon$ro generated in the first blade 111 when the external force Fy acts in the Y direction and when the acting force Ft from the gripping target acts have different signs. This is similar in the inner distortion $\Delta\varepsilon$li and the outer distortion $\Delta\varepsilon$lo generated in the second blade 112. Therefore, it is possible to extract the distortion amount component caused by the force Fz acting by the gripping target and the force Fy acting in the Y direction on the forceps unit 110 by taking the difference between the inner distortion $\Delta\varepsilon$ri and the outer distortion $\Delta\varepsilon$ro generated in the first blade 111 and the difference between the inner distortion $\Delta\varepsilon$li and the outer distortion $\Delta\varepsilon$lo generated in the second blade 112.

From above, with reference to FIG. 10, a process in the signal processing unit 1000 of converting the wavelength changes $\Delta\lambda$ri, $\Delta\lambda$ro, $\Delta\lambda$li, and $\Delta\lambda$lo detected from the optical fibers 511 to 514 into the force Fz acting in the long axis direction of the forceps unit 110 as the end effector and the total gripping force Fg is described.

A sum mode unit 1001 obtains a sum ($\Delta\lambda$ri+$\Delta\lambda$ro) of the inner and outer wavelength changes $\Delta\lambda$ri and $\Delta\lambda$ro detected from the optical fibers 511 and 512 attached to the first blade 111 and outputs a value obtained by dividing the same into two to a Fz deriving unit 1003 on a subsequent stage as $\Delta\lambda_{sum,r}$. Furthermore, the sum mode unit 1001 obtains a sum ($\Delta\lambda$li+$\Delta\lambda$lo) of the inner and outer wavelength changes $\Delta\lambda$li and $\Delta\lambda$lo detected from the optical fibers 513 and 514 attached to the second blade 112 and outputs a value obtained by dividing the same into two to a Fz deriving unit 1003 on a subsequent stage as $\Delta\lambda_{sum,l}$. However, the sum mode unit 1001 does not always output the values obtained by dividing the sum of the inner distortion and the outer distortion of the first blade 111 and that of the second blade 112 by two, respectively, and there also is a case of multiplying the same by a predetermined calibration gain derived by a calibration experiment or the like to output.

A difference mode unit 1002 obtains a difference ($\Delta\lambda$ri−$\Delta\lambda$ro) between the inner and outer wavelength changes $\Delta\lambda$ri and $\Delta\lambda$ro detected from the optical fibers 511 and 512 attached to the first blade 111 and outputs a value obtained by dividing the same into two to a Fg deriving unit 1004 on a subsequent stage as $\Delta\lambda_{diff,r}$. Furthermore, the difference mode unit 1002 obtains a difference ($\Delta\lambda$li−$\Delta\lambda$lo) between the inner and outer wavelength changes $\Delta\lambda$li and $\Delta\lambda$lo detected from the optical fibers 513 and 514 attached to the second blade 112 and outputs a value obtained by dividing the same into two to the Fg deriving unit 1004 on the subsequent stage as $\Delta\lambda_{diff,l}$. However, the difference mode unit 1002 does not always output the values obtained by dividing the difference between the inner distortion and the outer distortion of the first blade 111 and that of the second blade 112 by two, respectively, and there also is a case of multiplying the same by a predetermined calibration gain derived by a calibration experiment or the like to output.

A 4 DOF sensor unit 1005 is a functional module which calculates the translational forces Fx and Fy in the two directions and the moments Mx and My in the two directions acting on the end effector (forceps unit 110) on the basis of the detection signal of the 4 DOF sensor formed in the first link 210 in the signal processing unit 1000. A procedure for calculating the translational forces Fx and Fy in the two directions and the moments Mx and My in the two directions in the 4 DOF sensor unit 1005 is described later in detail. Here, it should be noted that Fx which is one of the translational forces calculated by the 4 DOF sensor unit 1005 is input to the Fz deriving unit 1003.

The dummy FBG processing unit 1006 obtains the sum of the detection values of the four dummy FBG sensors provided in the optical fibers 511 to 514 or the value obtained by multiplying the sum value by the calibration gain, and outputs the same to the Fz deriving unit 1003 as the wavelength change amount $\Delta\lambda_{dummy}$ detected by the dummy FBG sensor. Note that, the wavelength change of each dummy FBG sensor is caused by the temperature change (described above). However, it is assumed that the detecting unit detects the wavelength changes of the four dummy FBG sensors provided in the optical fibers 511 to 514.

The Fz deriving unit 1003 derives the translational force Fz acting in the long axis direction of the forceps unit 110 as the end effector by inputting the sum $\Delta\lambda_{sum,r}$ of the wavelength changes on the inner and outer sides of the first forceps unit 111 and the sum $\Delta\lambda_{sum,l}$ of the wavelength changes on the inner and outer sides of the second forceps unit 112 from the sum mode unit 1001, inputting the translational force Fx from the 4 DOF sensor unit 1005, and inputting the wavelength change amount $\Delta\lambda_{dummy}$ detected by the dummy FBG sensor from the dummy FBG processing unit 1006.

Here, Fz is a total force of the translational force frz acting in the long axis direction on the first blade 111 and the translational force flz acting in the long axis direction on the second blade 112 (in other words, Fz=frz+flz). On the other hand, $\Delta\lambda_{sum,r}$ and $\Delta\lambda_{sum,l}$ input from the sum mode unit 1001 include components caused by the translational forces Fz and Fx in the two directions acting on the forceps unit 110, respectively. Furthermore, since $\Delta\lambda_{sum,r}$ and $\Delta\lambda_{dummy}$ input from the sum mode unit 1001 take the sum of the distortion between the opposite sides of the first forceps unit 111 and the sum of the distortion between the opposite sides of the second blade 112, the wavelength change component $\Delta\lambda_{temp}$ caused by the temperature change remain.

Therefore, the Fz deriving unit 1003 obtains a distortion component (Fx/kx) caused by Fx by dividing the translational force Fx in the X direction input from the 4 DOF sensor unit 1005 by a calibration matrix kx which converts the wavelength change by Fx into the force. Then, the Fz deriving unit 1003 may calculate the sum of $\Delta\lambda_{sum,r}$ and $\Delta\lambda_{sum,l}$ input from the sum mode unit 1001, subtract the wavelength change component (Fx/kx) caused by Fx and the wavelength change component $\Delta\lambda_{dummy}$ caused by the temperature change input from the FBG processing unit 1006 from the sum, and multiply the same by a calibration matrix kz which converts the wavelength change into the force, thereby deriving the force Fz acting in the long axis direction of the forceps unit 110. Equation (1) for calculating Fz in the Fz deriving unit 1003 is described below. In the equation, kx represents the calibration matrix that converts the wavelength change due to the translational force Fx into the force, and kz represents the calibration matrix that converts the wavelength change due to the translational force Fz into the force.

[Equation 1]
$$F_z = f_{rz} + f_{lz} \qquad (1)$$
$$= \left(\Delta\lambda_{sum,r} + \Delta\lambda_{sum,l} - \frac{F_x}{k_z} - \Delta\lambda_{dummy}\right) \times k_z$$

The Fg deriving unit 1004 derives the total gripping force Fg of the forceps unit 110 which grips the gripping target by inputting the difference $\Delta\lambda_{diff,r}$ in wavelength change between the inner side and the outer side of the first forceps unit 111 and the difference $\Delta\lambda_{diff,l}$ in wavelength change between the inner side and the outer side of the second forceps unit 112 from the difference mode unit 1002.

Here, Fg is the total force of the translational forces fry and fly acting in the Y direction on the first blade 111 and the second blade 112, and frt and flt acting on the first blade 111 and the second blade 112 from the gripping target (in other words, Fg=frt+flt+fry−fly). On the other hand, the difference $\Delta\lambda_{diff,r}$ in the wavelength change on the first blade 111 side and the difference $\Delta\lambda_{diff,l}$ in the wavelength change on the second blade 112 side include the component caused by each of the translational force Fy acting in the Y direction on the forceps unit 110 and the acting force Ft from the gripping target. Furthermore, since $\Delta\lambda_{diff,r}$ and $\Delta\lambda_{diff,l}$ input from the difference mode unit 1002 take a difference in distortion between the opposite sides of the first forceps unit 111 and the difference in distortion between the opposite sides of the second blade 112, the wavelength change component $\Delta\lambda_{temp}$ caused by the temperature change is cancelled.

Therefore, the Fg deriving unit 1006 may calculates the sum of $\Delta\lambda_{diff,r}$ and $\Delta\lambda_{diff,l}$ input from the difference mode unit 1002 as represented by following equation (2), and further multiply a calibration matrix kt which converts the wavelength change by the acting force Ft from the gripping target to the force, thereby deriving the total gripping force Fg applied to the forceps unit 110.

[Equation 2]
$$F_g = f_{rt} + f_{lz} + f_{ry} - f_{ly} \qquad (2)$$
$$= (\Delta\lambda_{diff,r} + \Delta\lambda_{diff,l}) \times k_t$$

Note that the calibration matrices kx, kz, and kt used in the calculation of the signal processing unit 1000 illustrated in FIG. 10 may be derived, for example, by the calibration experiment.

In this manner, by applying the above-described arithmetic process by the signal processing unit 1000 to the surgical system 100, the 2 DOF sensor which detects the force acting on the forceps unit 110 as the end effector and the total gripping force Fg in the forceps unit 110 may be realized.

Figure 13:
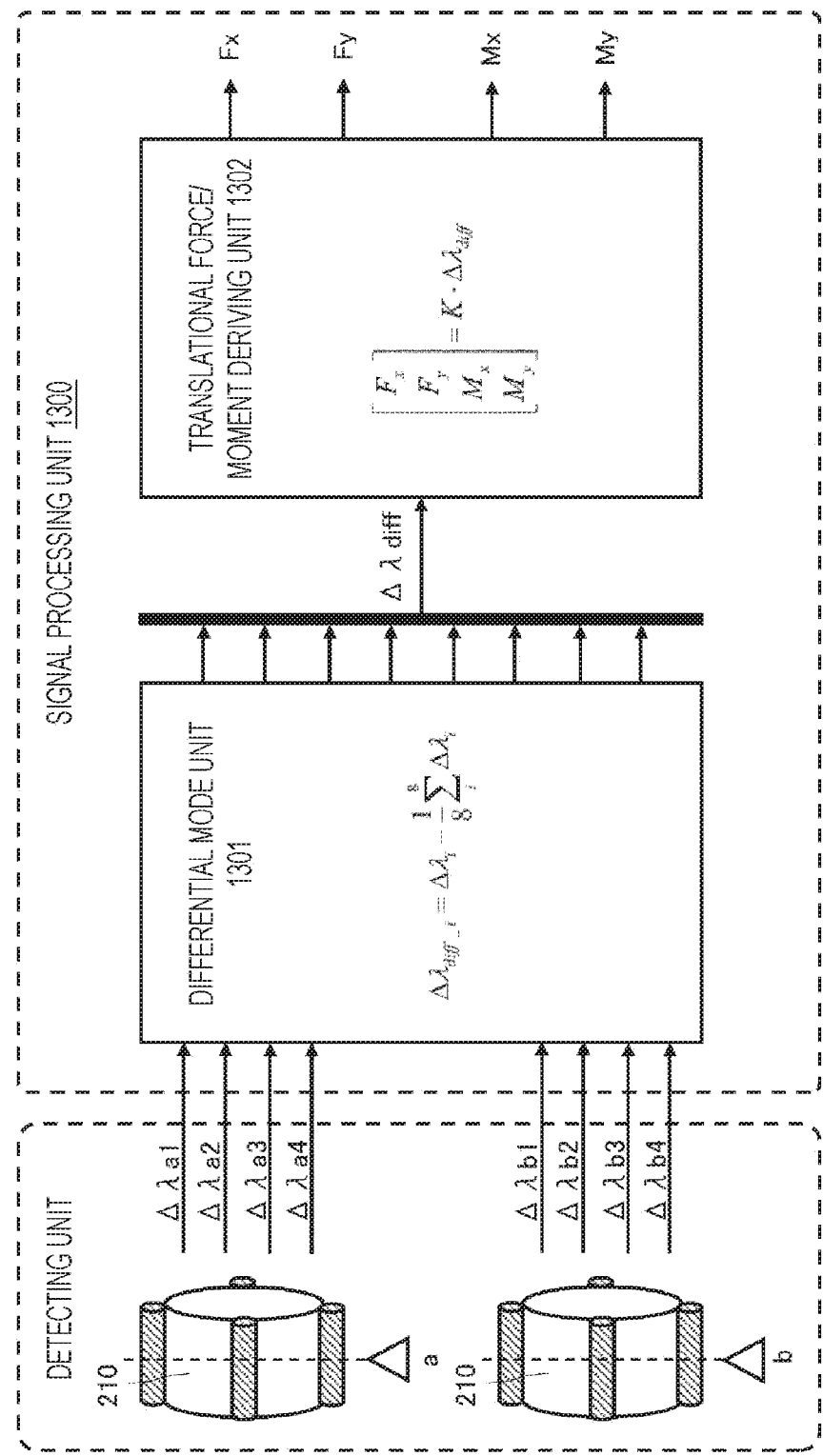
FIG. 13 is a view for explaining an algorithm of arithmetic process performed by a signal processing unit 1300.

FIG. 13 schematically illustrates the processing algorithm for the 4 DOF sensor for calculating the translational forces Fx and Fy in the two directions and the moments Mx and My acting on the end effector 110 on the basis of the detection results obtained from the FBG sensor formed on each of the optical fibers 901 to 904 laid on the first link 210 in the signal processing unit 1300. Note that, it should be understood that the signal processing unit 1300 illustrated in FIG. 13 corresponds to the 4 DOF sensor unit 1005 in FIG. 10.

The detecting unit detects wavelength changes $\Delta\lambda a1$ to $\Delta\lambda a4$ in the FBG sensors as the distortion detecting elements 211*a* to 214*a* arranged at the position a of the first link 210 when the translational forces Fx and Fv and the moments Mx and My act on the basis of the reflected light of the incident light of a predetermined wavelength band to the optical fibers 901 to 904 attached to the opposite sides in the XY directions of the first link 210. The detected wavelength changes $\Delta\lambda a1$ to $\Delta\lambda a4$ also include the wavelength change components caused by the temperature change.

Furthermore, the detecting unit detects wavelength changes $\Delta\lambda b1$ to $\Delta\lambda b4$ in the FBG sensors as the distortion detecting elements 211*b* to 214*b* arranged at the position b of the first link 210 when the translational forces Fx and Fy and the moments Mx and My act on the basis of the reflected light of the incident light of a predetermined wavelength band to the optical fibers 901 to 904 attached to the opposite sides in the XY directions of the first link 210. The detected wavelength changes Δλb1 to Δλb4 also include the wavelength change components caused by the temperature change.

Here, the wavelength changes Δλa1 to Δλa4 detected by the detecting unit from the position a of the optical fibers 901 to 904 are equivalent to distortion amounts Δεa1 to Δεa4 generated at the position a of the first link 210 when the translational forces Fx and Fy and the moments Mx and My act. Furthermore, wavelength changes Δλb1 to Δλb4 detected by the detecting unit from the position b of the optical fibers 901 to 904 are equivalent to distortion amounts Δεb1 to Δεb4 generated at the position b of the first link 210 when the translational forces Fx and Fy and the moments Mx and My act (in a case where the component of the wavelength change caused by the temperature change is ignored).

A differential mode unit 1301 subtracts an average value of eight inputs from each of the eight inputs of Δλa1 to Δλa4 and Δλb1 to Δλb4 from the detecting unit according to following equation (3), and outputs the same to a translational force/moment deriving unit 1302 on a subsequent stage. The wavelength change detected at each of the positions a and b includes the wavelength change component $\Delta\lambda_{sum,r}$ caused by the temperature change as well as the wavelength change component due to action distortion due to the translational forces Fx and Fy and the moments Mx and My. The differential mode unit 1301 may cancel the wavelength change component $\Delta\lambda_{temp}$ caused by the temperature change.

[Equation 3]

$$\Delta\lambda_{diff\_i} = \Delta\lambda_i - \frac{1}{8}\sum_{i}^{8}\Delta\lambda_i \quad (3)$$

Then, the translational force/moment deriving unit 1302 multiplies a calibration matrix K by the input $\Delta\lambda_{diff}$ from the differential mode unit 1301 as represented by following equation (4) to calculate the translational forces Fx and Fy and the moments Mx and My. Furthermore, the translational force Fx calculated by the translational force/moment deriving unit 1302 is input to the Fz deriving unit 1003 for calculating Fz (described above).

[Equation 4]

$$\begin{bmatrix} F_x \\ F_y \\ M_x \\ M_y \end{bmatrix} = K \cdot \Delta\lambda_{diff} \quad (4)$$

Note that the calibration matrix K used in the calculation of the signal processing unit 1300 illustrated in FIG. 13 may be derived, for example, by the calibration experiment.

The signal processing unit 1000 illustrated in FIG. 10 and the signal processing unit 1300 illustrated in FIG. 13 may be configured as one circuit chip, or may be configured as different circuit chips.

In this manner, according to this embodiment, the surgical system 100 may detect the translational force Fz and the acting force Ft from the gripping target by the 2 DOF sensor formed in the end effector 110 (refer to FIG. 10) and detect the two translational forces Fx and Fy and the two moments Mx and My by the 4 DOF sensor formed in the first link 210 (refer to FIG. 13). Therefore, it may also be said that the entire surgical system 100 is equipped with a (5+1) DOF sensor (or 6 DOF sensor).

For example, in a case where the surgical system 100 operates as a slave device in the master-slave robot system, the detection result by the (5+1) DOF sensor described above is transmitted to a master device as feedback information for remote control. On the master device side, the feedback information may be used for various applications. For example, the master device may perform force presentation to the operator on the basis of the feedback information from the slave device.

Figure 14:
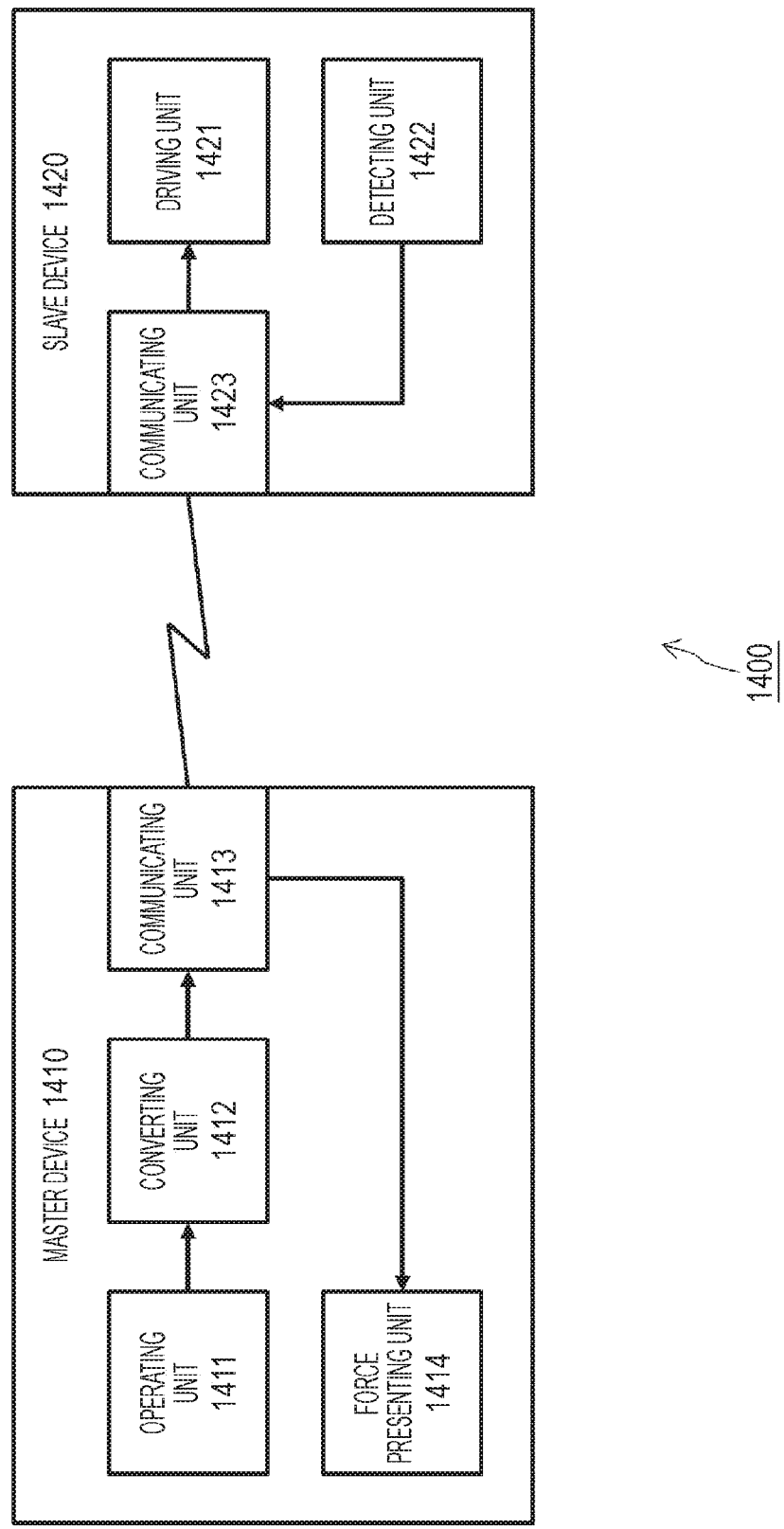
FIG. 14 is a view illustrating a functional configuration of a master-slave robot system 1400.

FIG. 14 schematically illustrates a functional configuration of a master-slave robot system 1400. The robot system 1400 includes a master device 1410 operated by the operator and a slave device 1420 remotely controlled from the master device 1410 according to the operation by the operator. The master device 1410 and the slave device 1420 are interconnected via a wireless or wired network.

The master device 1410 includes an operating unit 1411, a converting unit 1412, a communicating unit 1413, and a force presenting unit 1414.

The operating unit 1411 includes a master arm or the like for the operator to remotely control the slave device 1420. The converting unit 1412 converts a content of the operation performed by the operator on the operating unit 1411 into control information for controlling drive of the slave device 1420 side (more specifically, a driving unit 1421 in the slave device 1420).

The communicating unit 1413 is interconnected to the slave device 1420 side (more specifically, a communicating unit 1423 in the slave device 1420) via a wireless or wired network. The communicating unit 1413 transmits the control information output from the converting unit 1412 to the slave device 1420.

On the other hand, the slave device 1420 includes the driving unit 1421, a detecting unit 1422, and the communicating unit 1423.

The slave device 1420 is assumed to be an arm type robot having a multi-link configuration to a tip end of which the end effector such as the forceps unit 110 is attached as illustrated in FIG. 1. The driving unit 1421 includes an actuator for rotationally driving each joint connecting the links, and an actuator for opening and closing the forceps unit 110. The actuator for opening and closing the forceps unit 110 is arranged at a location apart from the forceps unit 110, and a driving force is transmitted to the forceps unit 110 by a cable.

The detecting unit 1422 includes the 2 DOF sensor formed in the forceps unit 110 and the 4 DOF sensor formed in the first link 210 (or other links). In other words, the detecting unit 1422 is the (5+1) DOF sensor capable of detecting the acting force Ft from the gripping target to the forceps unit 110 in addition to the translational forces Fx, Fy, and Fx in the three directions and the moments Mx and My about the XY axes acting on the forceps unit 110 as the end effector.

The communicating unit 1423 is interconnected to the master device 1410 side (more specifically, the communicating unit 1413 in the master device 1420) via a wireless or wired network. The driving unit 1421 described above drives according to the control information received by the communicating unit 1423 from the master device 1410 side. Furthermore, the detection results (Fx, Fy, Fz, Mx, My, and Ft) by the above-described detecting unit 1422 are transmitted from the communicating unit 1423 to the master device 1410 side.

On the master device 1410 side, the force presenting unit 1414 performs force presentation to the operator on the basis of the detection results (Fx, Fy, Fz, Mx, My, and Ft) received by the communicating unit 1413 as the feedback information from the slave device 1420.

The operator operating the master device 1410 may recognize a contact force applied to the end effector on the slave device 1420 side through the force presenting unit 1414. For example, in a case where the slave device 1420 is a surgical robot, the operator may appropriately perform manual operation when operating suture by obtaining a tactile sensation such as a response acting on the forceps unit 110, and completes suturing completely, so that it is possible to work efficiently while preventing invasion to living tissue.

INDUSTRIAL APPLICABILITY

The technology disclosed in this specification is heretofore described in detail with reference to the specific embodiment. However, it is obvious that one skilled in the art may modify or substitute the embodiment without departing from the scope of the technology disclosed in this specification.

The technology disclosed in this specification may be similarly applied to various types of robot devices other than the master-slave type. Furthermore, although the embodiment in which the technology disclosed in this specification is principally applied to the surgical robot is mainly described in this specification, the gist of the technology disclosed in this specification is not limited thereto; this may also be similarly applied to robot devices used in medical applications other than operation or various fields other than medical applications.

In short, the technology disclosed in this specification is heretofore described in a form of an example and the content described in this specification should not be interpreted in a limited manner. In order to determine the gist of the technology disclosed in this specification, claims should be taken into consideration.

Note that, the technology disclosed in this specification may also have the following configuration.

(1) An operation system including:
an arm including one or more links;
an end effector arranged at a tip end of the arm;
a first distortion detecting unit that detects distortion generated in the end effector;
a second distortion detecting unit that detects distortion generated in the link; and
a processing unit that calculates a force acting on the end effector on the basis of detection results of the first distortion detecting unit and the second distortion detecting unit.

(2) The operation system according to (1) described above,
in which the end effector includes a forceps unit including a first blade, a second blade, and a joint that defines a forceps rotational axis, the joint coupling the first blade and the second blade so as to be rotatable with respect to each other.

(3) The operation system according to (2) described above,
in which a distortion generating body is formed on each of the first blade and the second blade, and
the first distortion detecting unit includes distortion detecting elements arranged on distortion generating bodies of the first blade and the second blade.

(4) The operation system according to (3) described above,
in which the first distortion detecting unit includes distortion detecting elements that detect distortion generated on an inner side and an outer side of the first blade, and distortion detecting elements that detect distortion generated on an inner side and an outer side of the second blade, and
the processing unit calculates a force acting on the end effector on the basis of the distortion on the inner side and the outer side of the first blade and the distortion on the inner side and the outer side of the second blade which are detected.

(5) The operation system according to (4) described above,
in which the first distortion detecting unit includes distortion detecting elements including FBG sensors formed on optical fibers attached to the inner side and the outer side of the first blade, and distortion detecting elements including FBG sensors formed on optical fibers attached to the inner side and the outer side of the second blade.

(6) The operation system according to (4) or (5) described above,
in which the processing unit calculates a force acting in a long axis direction of the end effector on the basis of a sum of the distortion on the inner sides of the first blade and the second blade and of the distortion on the outer sides of the first blade and the second blade.

(7) The operation system according to (6) described above,
in which the processing unit removes a distortion component caused by a force acting in a direction orthogonal to the long axis direction of the end effector calculated on the basis of the detection result of the second distortion detecting unit from a value based on the sum, and calculates the force acting in the long axis direction of the end effector.

(8) The operation system according to (6) or (7) described above,
in which the processing unit removes a distortion component caused by a temperature change from a value based on the sum, and calculates the force acting in the long axis direction of the end effector.

(9) The operation system according to (8) described above,
in which the first distortion detecting unit includes distortion detecting elements including FBG sensors formed on optical fibers attached to the inner side and the outer side of the first blade, and distortion detecting elements including FBG sensors formed on optical fibers attached to the inner side and the outer side of the second blade, the optical fibers including dummy FBG sensors formed thereon, and
the processing unit removes a distortion component caused by a temperature change from a value based on the sum on the basis of a wavelength change of the dummy FBG sensors.

(10) The operation system according to any one of (4) to (9) described above,
in which the processing unit calculates the force acting in the long axis direction of the end effector on the basis of a difference between the distortion on the inner sides of the first blade and the second blade and the distortion on the outer sides of the first blade and the second blade.

(11) The operation system according to any one of (1) to (10) described above,
in which the second distortion detecting unit includes distortion detecting elements arranged at two locations on opposite sides in two directions orthogonal to the long axis direction of the link, and the processing unit calculates translational forces and moments in two directions acting on the end effector on the basis of the distortion at the two locations on the opposite sides in the two directions orthogonal to a long axis direction of the link detected by the second distortion detecting elements.

(12) The operation system according to (11) described above, in which the second distortion detecting unit includes the distortion detecting elements including FBG sensors formed in the two locations of optical fibers attached to the opposite sides in the two directions orthogonal to the long axis direction of the link.

(13) The operation system according to (11) or (12) described above, in which the link has a shape in which stress is concentrated at the two locations where the distortion detecting elements are arranged.

(14) The operation system according to any one of (11) to (13) described above, in which the processing unit obtains an average value of detection values of the distortion detecting elements, multiplies a result obtained by subtracting the average value from the detection values of the distortion detecting elements by a predetermined calibration matrix, and calculates translational forces and moments in the two directions acting on the end effector.

(15) The operation system according to any one of (1) to (14) described above, further including:

a driving unit arranged apart from the end effector; and
cables that transmit a driving force generated by the driving unit to the first blade and the second blade.

(16) A surgical system including:

a master device; and a slave device remotely operated by the master device, the slave device including:
an arm including one or more links;
an end effector arranged at a tip end of the arm;
a first distortion detecting unit that detects distortion generated in the end effector;
a second distortion detecting unit that detects distortion generated in the link;
a processing unit that calculates a force acting on the end effector on the basis of detection results of the first distortion detecting unit and the second distortion detecting unit, and
an output unit that outputs a processing result by the processing unit to the master device.

(17) A control device including:

a processing unit that calculates a force acting on the end effector on the basis of distortion generated on an end effector arranged at a tip end of an arm and distortion generated on a link forming the arm.

(18) A distortion generating body including:

a structure body formed as a blade of a forceps; and
a distortion generating unit obtained by forming a meander structure in a long axis direction of the structure body,
in which distortion detecting elements are attached on an inner side and an outer side of an opening/closing structure of the forceps of the distortion generating unit.

(19) A surgical instrument including:

an arm including one or more links;
an end effector arranged at a tip end of the arm;
a first distortion detecting unit that detects distortion generated in the end effector;
a second distortion detecting unit that detects distortion generated in the link; and a transmitting unit that transmits detection results of the first distortion detecting unit and the second distortion detecting unit.

(20) An external force detecting system including:

an arm including one or more links;
an end effector arranged at a tip end of the arm;
a first distortion detecting unit that detects distortion generated in the end effector;
a second distortion detecting unit that detects distortion generated in the link; and
a processing unit that calculates a force acting on the end effector on the basis of detection results of the first distortion detecting unit and the second distortion detecting unit.

REFERENCE SIGNS LIST

100 Surgical system
110 End effector (forceps unit)
111 First blade
112 Second blade
113 Forceps rotational axis
120 Articulated arm
201 to 204 Distortion detecting element
401 Distortion generating body
501, 502 Groove
511 to 514 Optical fiber
701, 702 Dummy FBG sensor
901 to 904 Optical fiber
1000 Signal processing unit
1001 Sum mode unit
1002 Difference mode unit
1003 Fz deriving unit
1004 Fg deriving unit
1005 4 DOF sensor unit
1006 Dummy FBG processing unit
1300 Signal processing unit
1301 Differential mode unit
1302 Translational force/moment deriving unit
1400 Robot system
1410 Master device
1411 Operating unit
1412 Converting unit
1413 Communicating unit
1414 Force presenting unit
1420 Slave device
1421 Driving unit
1422 Detecting unit
1423 Communicating unit

The invention claimed is:

1. An operation system comprising:
an arm including one or more links;
an end effector arranged at a tip end of the arm, the end effector including a forceps;
a joint between the end effector and the tip end of the arm, the joint defining a forceps rotational axis,
a first distortion detector that detects distortion generated in the end effector;
a second distortion detector that detects distortion generated in the link; and
a processor configured to calculate a force acting on the end effector on a basis of detection results of the first distortion detector and the second distortion detector, wherein
the forceps include a first blade and a second blade, the joint coupling the first blade and the second blade so as to be rotatable with respect to each other around the forceps rotational axis, a distortion generating body includes a first distortion generating body on the first blade and a second distortion generating body on the second blade, the first distortion detector includes a plurality of first distortion detecting elements on the first distortion generating body of the first blade and a plurality of second distortion detecting elements arranged on the second distortion generating body the second blade, the first plurality of distortion detecting elements include an inner first distortion detecting element that detects distortion generated on an inner side of the first blade and an outer first distortion detecting element an outer side of the first blade, the second plurality of distortion detecting elements include an inner second distortion detecting element that detects distortion generated on an inner side of the second blade and an outer second distortion detecting element that detects distortion generated on an outer side of the second blade, the inner first distortion detecting element includes a fiber Bragg grating sensor formed on an optical fiber attached to the inner side of the first blade, the outer first distortion detecting element unit includes a fiber Bragg grating sensor formed on an optical fiber attached to the outer side of the first blade, the inner second distortion detecting element includes a fiber Bragg grating sensor formed on an optical fiber attached to the inner side of the second blade, and the outer second distortion detecting element includes a fiber Bragg grating sensor formed on an optical fiber the outer side of the second blade, each of the optical fibers extend beyond the first and second blades and include dummy fiber Bragg grating sensors formed thereon, and the processor is configured to:
calculate a force acting on the end effector on a basis of the distortion on the inner side and the outer side of the first blade and the distortion on the inner side and the outer side of the second blade which are detected,
calculate a force acting in a long axis direction of the end effector on a basis of a sum of the distortion on the inner sides of the first blade and the second blade and of the distortion on the outer sides of the first blade and the second blade,
remove a distortion component caused by a temperature change from a value based on the sum on a basis of a wavelength change of the dummy fiber Bragg grating sensors, and
calculate the force acting in the long axis direction of the end effector.

2. The operation system according to claim 1, wherein the inner first distortion detecting element includes a fiber Bragg grating sensor formed on an optical fiber attached to the inner side of the first blade, the outer first distortion detecting element includes a fiber Bragg grating sensor formed on an optical fiber attached to the outer side of the first blade, the inner second distortion detecting element includes a fiber Bragg grating sensor formed on an optical fiber attached to the inner side of the second blade, and the outer second distortion detecting element includes a fiber Bragg grating sensor formed on an optical fiber the outer side of the second blade.

3. The operation system according to claim 1, wherein the processor is configured to remove a distortion component caused by a force acting in a direction orthogonal to the long axis direction of the end effector calculated on a basis of the detection result of the second distortion detector from a value based on the sum, and calculate the force acting in the long axis direction of the end effector.

4. The operation system according to claim 1, wherein the processor is configured to calculate a force acting in the long axis direction of the end effector on a basis of a difference between the distortion on the inner sides of the first blade and the second blade and the distortion on the outer sides of the first blade and the second blade.

5. The operation system according to claim 1, further comprising:
an actuator arranged apart from the end effector, and
first and second cables that transmit a driving force generated by the actuator to the first blade and the second blade.

6. An operation system, comprising:
an arm including one or more links:
an end effector including a forceps arranged at a tip end of the arm;
a joint between the end effector and the tip end of the arm, the joint defining a forceps rotational axis;
a first distortion detector that detects distortion generated in the end effector;
a second distortion detector that detects distortion generated in the link,
wherein the second distortion detector includes a first pair of distortion detecting elements arranged at a first and second locations on opposite sides of the link along a first direction orthogonal to a long axis direction of the link and a second pair of distortion detecting elements arranged at along a third and fourth locations on opposite sides of the link along a second direction orthogonal to the first direction and orthogonal to the long axis direction of the link; and
a processor configured to
calculate a force acting on the end effector on a basis of detection results of the first distortion detector and the second distortion detector,
calculate translational forces and moments in two directions acting on the end effector on a basis of the distortion detected by the first and second pairs of distortion detecting elements, and
obtain an average value of detection values of the first and second pairs of the distortion detecting elements, multiply a result obtained by subtracting the average value from the detection values of the first and second pairs of the distortion detecting elements by a predetermined calibration matrix, and calculate translational forces and moments in the first and second directions acting on the end effector.

7. The operation system according to claim 6, wherein the first pair of distortion detecting elements each include a fiber Bragg grating sensor formed on an optical fiber, and
the second pair of distortion detecting elements each include a fiber Bragg grating sensor formed on an optical fiber.

8. The operation system according to claim 6, wherein the first and second locations and the third and fourth locations are where stress on the link is concentrated.

9. The operation system according to claim 6, wherein the second distortion detector includes a third pair of distortion detecting elements arranged at fifth and sixth locations on opposite sides of the link along the first direction and a fourth pair of distortion detecting elements arranged at along seventh and eighth locations on opposite sides of the link along the second direction orthogonal to the first direction and orthogonal to the long axis direction of the link, and
the processor is configured to calculate translational forces and moments in two directions acting on the end effector on a basis of the distortion detected by the first to fourth second pairs of distortion detecting elements.

* * * * *